US008241590B2

(12) United States Patent
Harada et al.

(10) Patent No.: US 8,241,590 B2
(45) Date of Patent: Aug. 14, 2012

(54) DISCHARGE VOLUME CONTROL METHOD, DISCHARGE PRESSURE CONTROL METHOD, AND MICROBODY FORMING METHOD

(75) Inventors: Tohru Harada, Kawasaki (JP); Akihiko Yabuki, Kawasaki (JP); Kiyoshi Taninaka, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 13/354,808

(22) Filed: Jan. 20, 2012

(65) Prior Publication Data

US 2012/0111886 A1    May 10, 2012

Related U.S. Application Data

(62) Division of application No. 11/785,431, filed on Apr. 17, 2007, now Pat. No. 8,124,031.

(30) Foreign Application Priority Data

Sep. 29, 2006  (JP) ................................. 2006-270053

(51) Int. Cl.
    *B01L 3/02*      (2006.01)
(52) U.S. Cl. ........ 422/521; 422/112; 422/114; 422/504; 435/286.1; 435/286.6; 73/864.11; 137/14; 137/47; 137/206; 137/565.01
(58) Field of Classification Search ............. 137/14, 137/47, 206, 565.01
    See application file for complete search history.

(56) References Cited

U.S. PATENT DOCUMENTS

| 4,532,205 | A | * | 7/1985 | Ansorge | 435/30 |
| 4,836,244 | A | * | 6/1989 | Ansorge | 137/557 |
| 5,225,750 | A | | 7/1993 | Higuchi et al. | |
| 5,456,880 | A | | 10/1995 | Miura | |
| 5,630,706 | A | | 5/1997 | Yang | |

FOREIGN PATENT DOCUMENTS

DE        44 01 076         7/1995
(Continued)

OTHER PUBLICATIONS

Canadian Office Action for corresponding Canadian application 2,586,746; dated Sep. 10, 2009. Japanese Office Action for corresponding Japanese Application 2006-270053; mailed Dec. 6, 2011.

(Continued)

*Primary Examiner* — In Suk Bullock
*Assistant Examiner* — Timothy G Kingan
(74) *Attorney, Agent, or Firm* — Staas & Halsey LLP

(57) ABSTRACT

A second valve is opened to combine an injection-pressure generating pressure with a maintaining pressure into an injection pressure. After the injection pressure is applied to a capillary to cause discharge of an object therefrom, an output pressure of a regulator is set to the injection pressure. Then, a first valve is opened to reapply the injection pressure to the capillary. The second valve is opened to combine a maintaining-pressure generating pressure with the injection pressure into the maintaining pressure. After the maintaining pressure is applied to the capillary to terminate the discharge of the object, the output pressure of the regulator is set to the maintaining pressure. Then, the first valve is opened to reapply the maintaining pressure to the capillary.

3 Claims, 16 Drawing Sheets

FOREIGN PATENT DOCUMENTS

| | | |
|---|---|---|
| JP | 57-051981 | 3/1982 |
| JP | 61-088066 | 5/1986 |
| JP | 3-119989 | 5/1991 |
| JP | 07-167846 | 7/1995 |
| JP | 10-267006 | 10/1998 |
| JP | 3-63897 | 6/1999 |
| JP | 11-212652 | 8/1999 |
| JP | 2000-019184 | 1/2000 |
| JP | 2001-000931 | 1/2001 |
| JP | 2001-187145 | 7/2001 |
| JP | 2002-272398 | 9/2002 |

OTHER PUBLICATIONS

U.S. Office Action for U.S. Appl. No. 11/785,431; mailed Nov. 5, 2010.

U.S. Office Action for U.S. Appl. No. 11/785,431; mailed Feb. 16, 2011.

U.S. Notice of Allowance for U.S. Appl. No. 11/785,431; mailed Oct. 24, 2011.

European Office Action for corresponding European Application 07106273.1-1521; dated May 16, 2012.

\* cited by examiner

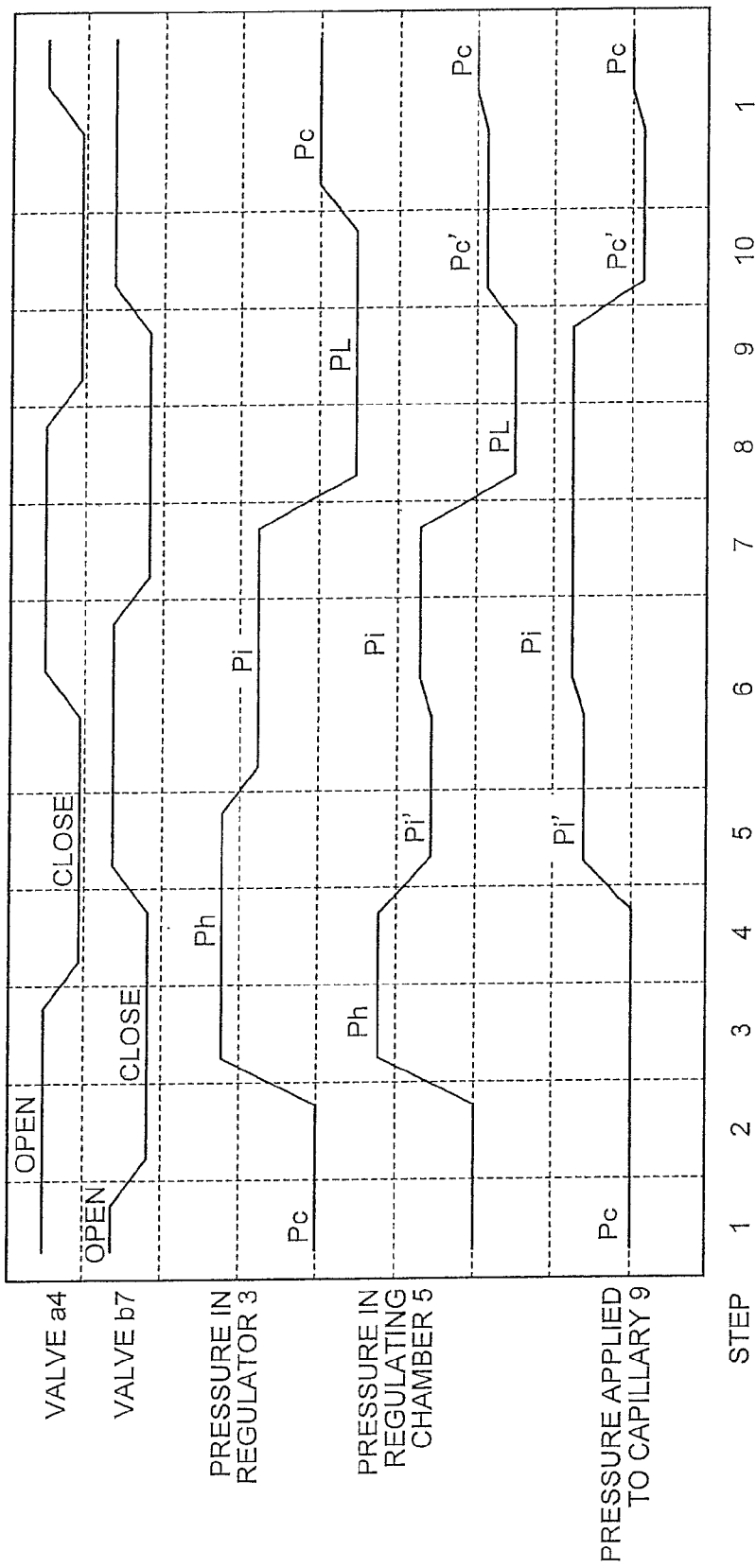

FIG.13

| (1) EQUATION | $P=(P1+\eta P2)/(\eta+1)$ |
|---|---|
| (2) EQUATION | $\eta = V2/V1 = (P1-P)/(P-P2)$ |
| (3) EQUATION | $P2=((\eta+1)P-P1)/\eta$ |

FIG.14

$$P_n = P_0 + \sum_{k=1}^{n} D_k$$

DISCHARGE VOLUME CONTROL METHOD, DISCHARGE PRESSURE CONTROL METHOD, AND MICROBODY FORMING METHOD

CROSS-REFERENCE TO RELATED APPLICATIONS

This application is a divisional of and claims the benefit of U.S. application Ser. No. 11/785,431, filed Apr. 17, 2007 now U.S. Pat. No. 8,124,031, and claims benefit under 35 U.S.C. Section 119 of Japanese Patent Application No. 2006-270053, filed Sep. 29, 2006 the disclosures of all of which are incorporated herein by reference.

BACKGROUND

1. Field

The present invention relates to a discharge volume control method, a discharge pressure control method, an injecting apparatus, a microbody forming method, a discharge volume control device, and a discharge volume control program 2. Description of the Related Art A microinjection, which is a method of injecting a specific substance (DNA, a drug, or the like) into a cell under a microscope, has been known in the fields of regenerative medicine, new drug designing, and the like. Microinjection is a method of pressurizing a capillary filled with a solution containing a predetermined substance in advance, thereby discharging the solution into a cell penetrated by the capillary to inject the substance into the cell. This method allows, for example, to examine effects of the injected substance on the cell. A quantitative discharge of a solution into a cell is critically important for microinjection. Therefore, liquid discharge volume control methods for regulating a discharge volume conveniently and accurately with high repeatability have been developed.

For example, Japanese Patent Application Laid-open No. H3-119989 (Paragraphs 0010 to 0014, FIG. 1, and FIG. 2) discloses a microinjection apparatus in which a male screw is rotated to move a plunger, thereby pressurizing a capillary to discharge liquid. Specifically, when an operator presses a button provided on a control box included in the microinjection apparatus, an electric signal is generated, and the generated electric signal causes a piezoelectric element to produce a drive force to rotate the female screw so that the plunger is moved to discharge liquid filled in the capillary. Accordingly, the operator of the microinjection apparatus achieves the discharge of the liquid out of the capillary penetrated into a cell conveniently at the simple push of the button.

While the conventional technology described above achieves discharge of liquid conveniently by moving a plunger with the push of a button, a discharge volume is regulated by an operator of the microinjection apparatus who observes a cell penetrated by the capillary under a microscope and estimates the discharge volume based on a degree of expansion of the cell to determine whether a predetermined liquid volume has been discharged. Therefore, the conventional technology still has a problem of not attaining a quantitative discharge of the liquid.

SUMMARY

It is an object of the present invention to at least partially solve the problems in the conventional technology.

According to an aspect of the present invention, a discharge volume control method for controlling a microinjection apparatus that includes a regulator regulating and outputting pressure, a capillary filled with an object to be discharged and connected to the regulator by a tube, a first valve located on regulator side in the tube and a second valve located on capillary side in the tube, and controlling volume of the object discharged from the capillary, includes opening the second valve from a state where the first valve and the second valve are closed to combine an injection-pressure generating pressure with a maintaining pressure to generate an injection pressure, the injection-pressure generating pressure being retained between the first valve and the second valve to generate the injection pressure that causes the object to be discharged from the capillary, and the maintaining pressure having been applied to the capillary to prevent backflow of the object into the capillary, applying the injection pressure to the capillary to cause discharge of the object from the capillary, setting an output pressure of the regulator to the injection pressure, opening the first valve to reapply the injection pressure to the capillary, opening the second valve from the state where the first valve and the second valve are closed to combine a maintaining-pressure generating pressure with the injection pressure having been applied to the capillary to generate the maintaining pressure, the maintaining-pressure generating pressure being retained between the first valve and the second valve to generate the maintaining pressure, applying the maintaining pressure to the capillary to terminate the discharge of the object, setting the output pressure of the regulator to the maintaining pressure, and opening the first valve to reapply the maintaining pressure to the capillary.

According to another aspect of the present invention, a discharge pressure control method for controlling pressure to discharge an object from a capillary connected to a pressure regulator and injecting the object into a microbody, includes closing a first valve that is located between the pressure regulator and the capillary in a state where pressure in the capillary is maintained at a first pressure, the pressure regulator generating a second pressure, closing a second valve that is located between the pressure regulator and the first valve, opening the first valve to combine the first pressure with the second pressure to generate a third pressure, applying the third pressure to the capillary to cause discharge of the object from the capillary, the pressure regulator resetting the third pressure, opening the second valve, closing the first valve, the pressure regulator generating a fourth pressure, closing the second valve, and opening the first valve to maintain the pressure in the capillary at the first pressure.

According to still another aspect of the present invention, a discharge pressure control method for controlling pressure to discharge an object from a capillary connected to a pressure regulator and injecting the object includes closing a first valve that is located between the pressure regulator and the capillary in a state where pressure in the capillary is maintained at a first pressure, the pressure regulator generating a second pressure, closing a second valve that is located between the pressure regulator and the first valve, opening the first valve to combine the first pressure with the second pressure to generate a third pressure, applying the third pressure to the capillary to cause discharge of the object from the capillary, and the pressure regulator resetting the third pressure in a state where the object has been discharged from the capillary.

According to still another aspect of the present invention, a discharge pressure control method for controlling pressure to discharge an object from a capillary connected to a pressure regulator, includes the pressure regulator generating a second pressure in a state where pressure in the capillary is maintained at a first pressure, combining the first pressure with the second pressure to generate a third pressure, applying the third pressure to the capillary to cause discharge of the object from the capillary, the pressure regulator resetting the third pressure while the object is being discharged from the capillary, and maintaining the pressure in the capillary at the third pressure.

According to still another aspect of the present invention, a discharge pressure control method for controlling pressure to discharge an object from a capillary connected to a pressure regulator, includes closing a valve that is located in a passage between the pressure regulator and the capillary in a state where pressure in the capillary is maintained at a predetermined pressure, measuring pressure in the passage between the valve and the capillary with a pressure gauge that is located between the valve and the capillary, and indicating a result of the measurement when the pressure falls below a predetermined threshold value during a predetermined time period.

According to still another aspect of the present invention, an injecting apparatus that injects an object into a microbody, includes a capillary that injects the object into the microbody, a regulator that regulates pressure to be applied to the object, a first valve that is located in a passage between the capillary and the regulator, a second valve that is located between the first valve and the regulator, and a controller that controls the regulator, the first valve, and the second valve. The controller closes the first valve in a state where pressure in the capillary is maintained at a first pressure, causes the regulator to generate a second pressure, and closes the second valve. The controller then opens the first valve to combine the first pressure with the second pressure to generate a third pressure, applies the third pressure to the capillary to cause discharge of the object from the capillary, and causes the regulator to reset the third pressure while the object is being discharged from the capillary.

According to still another aspect of the present invention, a microbody forming method for forming a microbody into which a capillary injects an object, includes inserting the capillary into the microbody in a state where pressure in the capillary is maintained at a first pressure, a regulator generating a second pressure, combining the first pressure with the second pressure to generate a third pressure, applying the third pressure to the capillary to inject the object from the capillary into the microbody, the regulator resetting the third pressure while the object is being injected, maintaining the pressure in the capillary at the third pressure, the regulator generating a fourth pressure, maintaining the pressure in the capillary at the first pressure by application of the third pressure and a fourth pressure, and removing the capillary from the microbody.

According to still another aspect of the present invention, a discharge volume control device that controls a microinjection apparatus that includes a regulator regulating and outputting pressure, a capillary filled with an object to be discharged and connected to the regulator by a tube, a first valve located on regulator side in the tube and a second valve located on capillary side in the tube, and controls volume of the object discharged from the capillary, includes an injection pressure regulating unit that opens the second valve from a state where the first valve and the second valve are closed to combine an injection-pressure generating pressure with a maintaining pressure to generate an injection pressure, the injection-pressure generating pressure being retained between the first valve and the second valve to generate the injection pressure that causes the object to be discharged from the capillary, and the maintaining pressure having been applied to the capillary to prevent backflow of the object into the capillary, applies the injection pressure to the capillary to cause discharge of the object from the capillary, sets an output pressure of the regulator to the injection pressure, and opens the first valve to reapply the injection pressure to the capillary, and a maintaining pressure regulating unit that opens the second valve from a state where the first valve and the second valve are closed to combine a maintaining-pressure generating pressure with the injection pressure having been applied to the capillary to generate the maintaining pressure, the maintaining-pressure generating pressure being retained between the first valve and the second valve to generate the maintaining pressure, applies the maintaining pressure to the capillary to terminate the discharge of the object, sets the output pressure of the regulator to the maintaining pressure, and opens the first valve to reapply the maintaining pressure to the capillary.

According to still another aspect of the present invention, a computer-readable recording medium stores therein a computer program that causes a computer to implement the above method.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIGS. 2A to 2C are schematics for explaining an overview and features of a liquid discharge volume control device shown in FIG. 1;

FIG. 13 is a schematic for explaining calculations of injection-pressure generating pressure and maintaining-pressure generating pressure; and FIG. 14 is a schematic for explaining an accumulated error in consecutive discharging.

DETAILED DESCRIPTION

Exemplary embodiments of the present invention are explained in detail below with reference to the accompanying drawings.

First, an example of a microinjection apparatus is explained. As disclosed in Japanese Patent Application Laid-Open No. 2006-133512, "METHOD FOR DISCHARGING LIQUID INTO CELL AND MICROINJECTION APPARATUS" by the inventor of this application, a liquid discharge volume control method for regulating a discharge volume by switching between two pressures, i.e., a pressure (hereinafter, "injection pressure") by which a solution (object) is discharged into a cell (microbody) and a pressure (hereinafter, "maintaining pressure") by which backflow to a capillary is prevented, is available.

Figure 11:
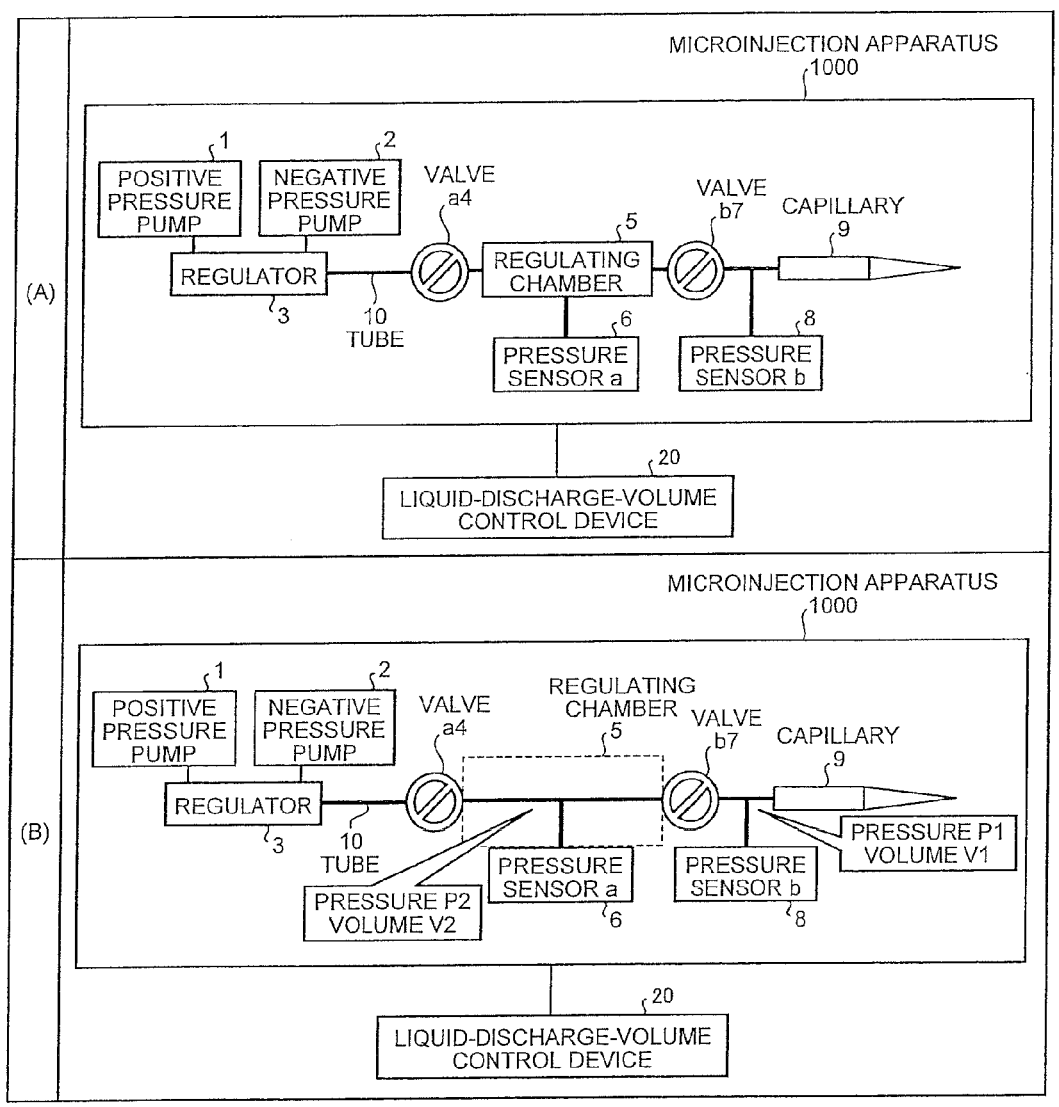
FIG. 11 is a schematic of a microinjection apparatus according to a conventional technology.

Specifically, in the conventional liquid discharge volume control method, a liquid volume to be discharged out of the capillary into a cell is quantitatively controlled by quickly generating an injection pressure in a state where the capillary receives a maintaining pressure so that discharge of liquid out of the capillary is started, and, after a lapse of a predetermined time, quickly reducing the pressure to the maintaining pressure to terminate the discharge of liquid out of the capillary. The conventional liquid discharge volume control method is briefly explained. FIG. 11 is a schematic of a microinjection apparatus 1000 according to the conventional technology. The microinjection apparatus 1000, which is connected to a positive pressure pump 1 and a negative pressure pump 2, includes a regulator 3, a regulating chamber 5, a capillary 9, a valve a4, a valve b7, a pressure sensor a6, and a pressure sensor b8. The regulator 3 maintains a pressure developed by the pumps 1 and 2 constant. The regulating chamber 5 traps the pressure maintained by the regulator 3. The capillary 9 is filled with a solution. The valve a4 is between the regulator 3 and the regulating chamber 5. The valve b7 is between the regulating chamber 5 and the capillary 9. The pressure sensor a6 detects a pressure in the regulating chamber 5. The pressure sensor b8 detects a pressure applied to the capillary. The regulator 3, the valve a4, the regulating chamber 5, the pressure sensor a6, the valve b7, the pressure sensor b8, and the capillary 9 are connected by a tube 10 (indicated by thick lines). A liquid-discharge-volume control device 20 that employs the liquid discharge volume control method controls operations of the microinjection apparatus 1000. For example, as each of the valves a4 and b7, a valve including an electromagnetic solenoid is employed. The liquid-discharge-volume control device 20 generates an electric signal, thereby controlling opening and closing operations of each of the valves a4 and b7.

In an actual configuration, rather than providing the regulating chamber 5 in the microinjection apparatus 1000, a portion of the tube 10 (the portion where the valve a4, the pressure sensor a6, and the valve b7 are connected), the portion indicated as an area surrounded by the dotted line in (B) of FIG. 11, forms the regulating chamber 5. Hereinafter, the regulating chamber 5 is the area surrounded by the dotted line in (B) of FIG. 11.

Figure 12A:
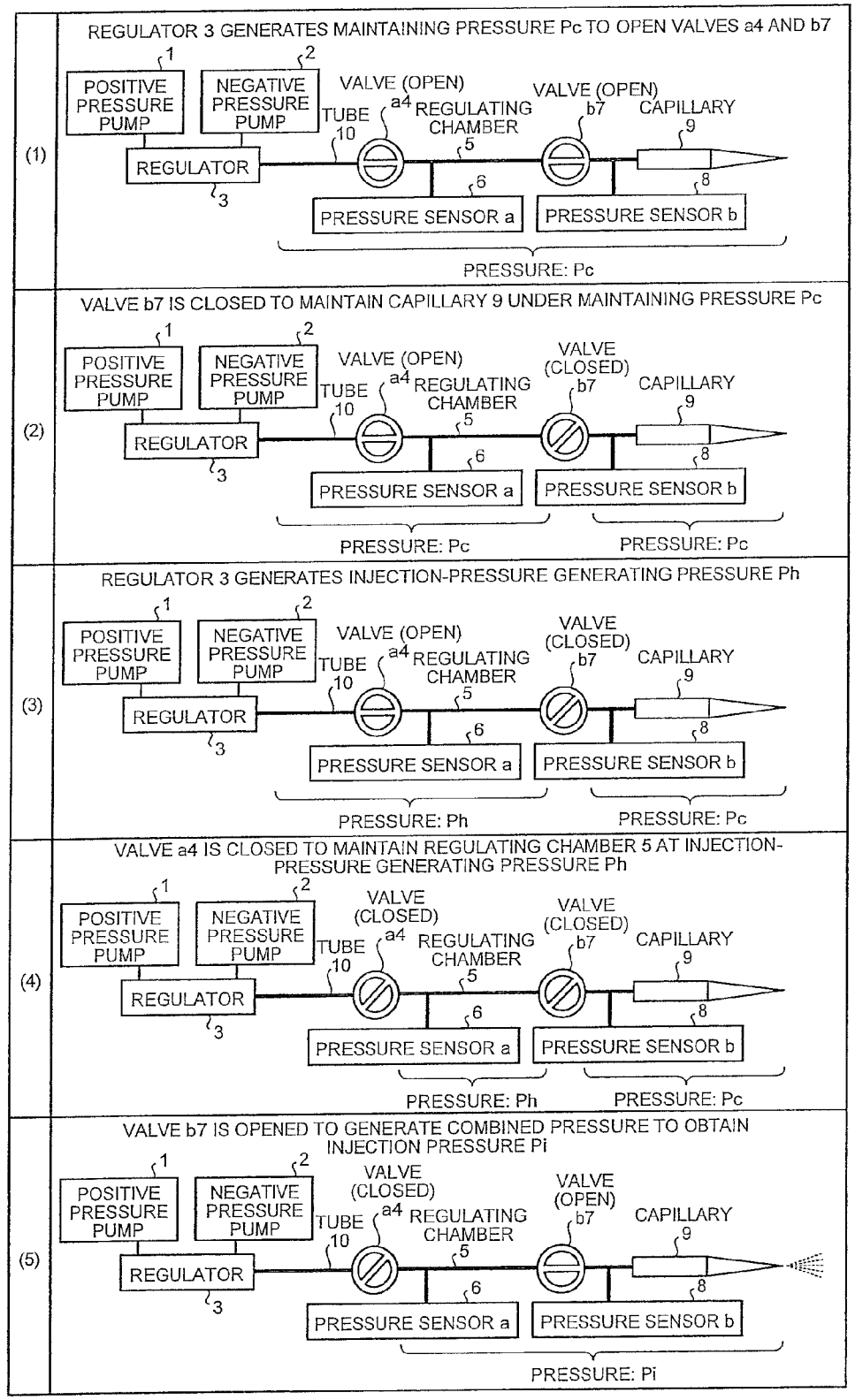
FIGS. 12A and 12B are schematics for explaining an overview and features of a liquid discharge volume control device shown in FIG. 11.
Figure 12B:
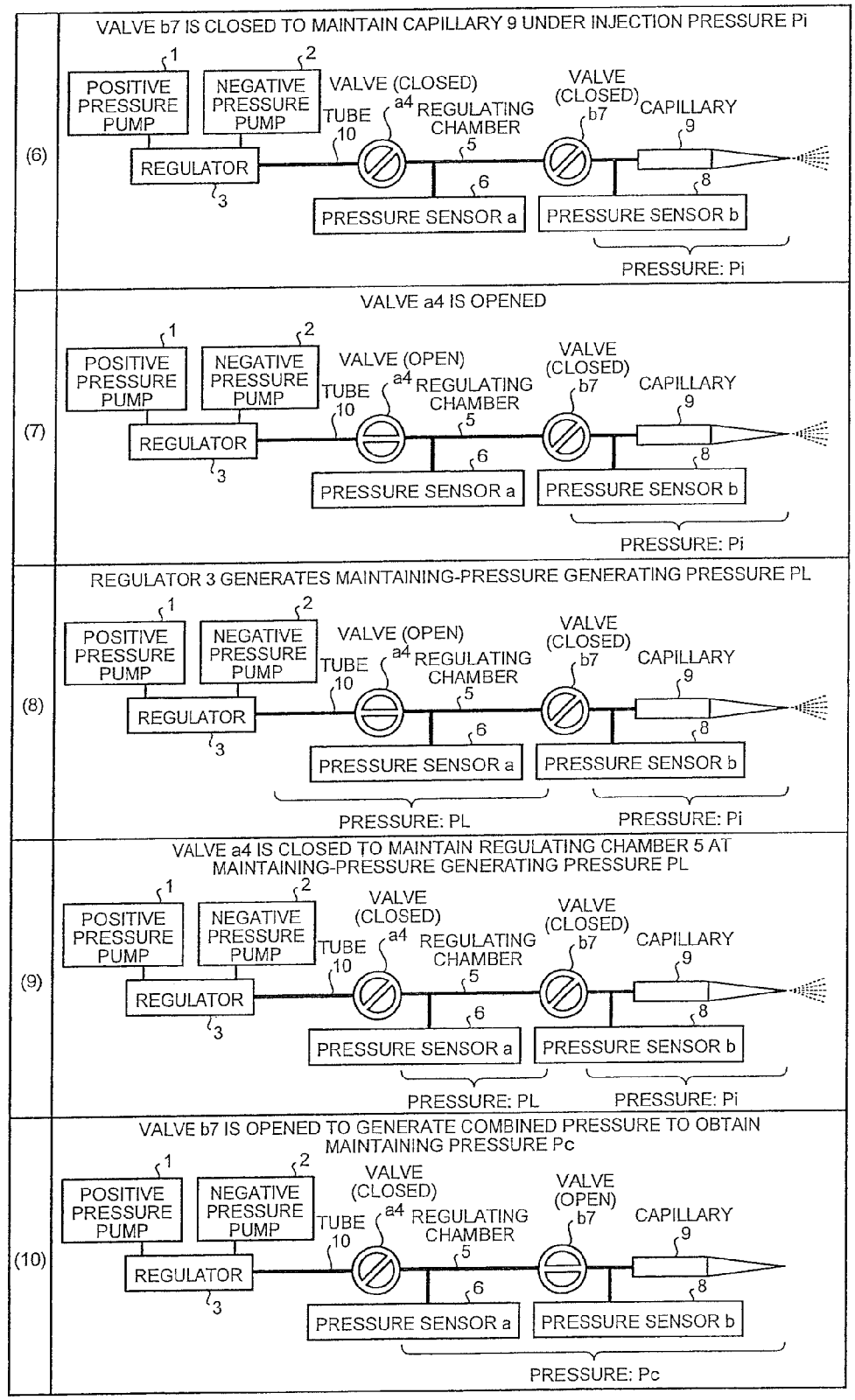

FIG. 12A and FIG. 12B are schematics for explaining an overview and features of the liquid discharge volume control device 20 according to the conventional technology.

First, with reference to FIG. 12A, steps that cover until application of an injection pressure Pi to the capillary 9 are explained. The liquid-discharge-volume control device 20 causes the regulator 3 to generate a maintaining pressure Pc by using the positive pressure pump 1 and the negative pressure pump 2, and then opens the valves a4 and b7 (see (1) of FIG. 12A). Subsequent to this step, an operator connects the capillary 9 filled with a solution to the tube 10. Hence, the liquid filled in the capillary 9 is retained in the capillary 9 without flowing backward. The state shown in (1) of FIG. 12A is maintained until penetration of a cell with the capillary 9 by the operator under a microscope to discharge the liquid becomes available.

When penetration of the cell with the capillary 9 by the operator to start injection becomes available, as shown in (2) of FIG. 12A, the liquid-discharge-volume control device 20 closes the valve b7 to maintain the capillary 9 under the maintaining pressure Pc in accordance with an operator request to start injection, and causes the regulator 3 to generate an injection-pressure generating pressure Ph (described later), which is a pressure necessary to generate the injection pressure Pi, by using the positive pressure pump 1 and the negative pressure pump 2 (see (3) of FIG. 12A).

As shown in (4) of FIG. 12A, the liquid-discharge-volume control device 20 closes the valve a4 to maintain the regulating chamber 5 under the pressure Ph, and then opens the valve b7. Consequently, the injection-pressure generating pressure Ph and the maintaining pressure Pc are combined into the injection pressure Pi to start liquid discharging (see (5) of FIG. 12A). As explained above, instantaneous opening/closing of the valves a4 and b7 allows to change the pressure applied to the capillary from the maintaining pressure Pc to the injection pressure Pi quickly.

Subsequently, with reference to FIG. 12B, steps that cover until the injection pressure Pi is reduced to the maintaining pressure Pc to terminate the discharge of liquid out of the capillary are explained. As shown in (6) of FIG. 12B, the liquid discharge volume control device 20 closes the valve b7 to maintain the capillary 9 under the injection pressure Pi, and opens the valve a4 (see (7) of FIG. 12B). The liquid-discharge-volume control device 20 then causes the regulator 3 to generate a maintaining-pressure generating pressure PL (described later), which is necessary to generate the maintaining pressure Pc, by using the positive pressure pump 1 and the negative pressure pump 2 (see (8) of FIG. 12B).

As shown in (9) of FIG. 12B, the liquid discharge volume control device 20 closes the valve a4 to maintain the regulating chamber 5 under the maintaining-pressure generating pressure PL, and then opens the valve b7 (see (10) of FIG. 12B). Consequently, the maintaining-pressure generating pressure PL and the injection pressure Pi are combined into the maintaining pressure Pc to terminate the discharge of liquid out of the capillary 9. As explained above, instantaneous opening/closing of the valves a4 and b7 allows to change the pressure applied to the capillary from the injection pressure to the maintaining pressure quickly. Accordingly, the injection pressure that takes a rectangular waveform can be applied to the capillary 9, which allows to perform accurate control of a liquid discharge volume by adjusting the injection pressure and an injection-pressure application time (a period of time required to perform steps (5) of FIG. 12A to (10) of FIG. 12B).

When the liquid-discharge-volume control device 20 is required to consecutively discharge liquid to another cell, the liquid-discharge-volume control device 20 causes the regulator 3 to generate the maintaining pressure Pc, and opens the valve a4 to shift the state from that shown in (10) of FIG. 12B to that shown in (1) of FIG. 12A, to perform operation control including the same steps as above. As explained above, even when injection is to be performed consecutively, it is possible to penetrate the capillary 9 into another cell and to shift to the injection stage under a pressure that is quickly reduced to the maintaining pressure Pc. Therefore, the liquid discharge volume can be accurately controlled also in the subsequent cycle.

The above-mentioned injection-pressure generating pressure Ph for generating the injection pressure Pi and the maintaining-pressure generating pressure PL for generating the maintaining pressure Pc are explained. A relation between a pressure at a point in time before the valve b7 is opened and a pressure at a point in time after the valve b7 is opened can be obtained using an equation of state of gas. As shown in (B) of FIG. 11, the gas volume on the capillary 9 side is denoted as V1, the pressure on the capillary 9 side at a point in time before the valve b7 is opened as P1, the gas volume of the regulating chamber 5 as V2, and the gas volume of the regulating chamber 5 at a point in time before the valve b7 is opened as P2. In this case, relations between the pressure P, which is a pressure at a point in time after the valve b7 is opened, and a volume ratio $\eta$ ($\eta=V2/V1$) are expressed by each of equations (1) and (2) of FIG. 13. Accordingly, a pressure P2 that need to be retained in the regulating chamber 5 before the valve b7 is opened to generate the pressure P after the valve b7 is opened can be expressed by equation (3) of FIG. 13.

Meanwhile, a pressure P1 on the capillary 9 side at a point in time before the valve b7 is opened can be obtained using the pressure sensor b8, the pressure P2 in the regulating chamber 5 at a point in time before the valve b7 is opened can be obtained using the pressure sensor a6, and the pressure P at a point in time after the valve b7 is opened can be obtained using the pressure sensors b7 and a6. Therefore, the volume ratio $\eta$ can be obtained in advance from equation (2) of FIG. 13 using the pressure values determined by performing a preliminary discharge of liquid.

The injection-pressure generating pressure Ph or the maintaining-pressure generating pressure PL is calculated using the volume ratio $\eta$ and equation (3) of FIG. 13. The injection-pressure generating pressure Ph is calculated by substituting the injection pressure Pi for the pressure P, which is the pressure at a point in time after the valve b7 is opened, and the maintaining pressure Pc for the pressure P1, which is the pressure on the capillary 9 side at a point in time before the valve b7 is opened, in equation (3) of FIG. 13. The maintaining-pressure generating pressure PL is calculated by substituting the maintaining pressure Pc for the pressure P, which is the pressure at a point in time after the valve b7 is opened, and the injection pressure Pi for the pressure P1, which is the pressure on the capillary 9 side at a point in time before the valve b7 is opened, in equation (3) of FIG. 13. The liquid-discharge-volume control device 20 causes the regulator 3 to generate the injection-pressure generating pressure Ph at step (3) of FIG. 12A, and the maintaining-pressure generating pressure PL at step (8) of FIG. 12B.

However, the above-explained method has a problem in that, even when the injection-pressure generating pressure Ph or the maintaining-pressure generating pressure PL is calculated, a change in the "volume ratio $\eta$" caused by elements such as flexibility of the material of the tube 10, pressure values, and a pressure-applying time develops a slight error in the target pressure in relation to at least one of an actually generated injection-pressure generating pressure Ph or an actually generated maintaining-pressure generating pressure PL, which results in unstable accuracy of the liquid discharge volume.

The above-explained method has another problem in that, because an error in an output of a regulator that regulates the pressure trapped in the regulating chamber 5 is not considered, when liquid is to be consecutively discharged on a cell-by-cell basis, errors in outputs are accumulated, which results in unstable accuracy of the liquid discharge volume. Put another way, in consecutive discharging, when an initial discharge pressure, a first discharge pressure, and a second discharge pressure are respectively denoted by $P_0$, $P_1$, and $P_2$, and errors between the pressures are denoted by D1 and D2 respectively, equations $P_1=P_0+D_1$ and $P_2=P_1+D_2$ hold. Accordingly, as shown in the equation of FIG. 14, an n-th discharge pressure includes an accumulated error corresponding to n times discharges.

Figure 1:
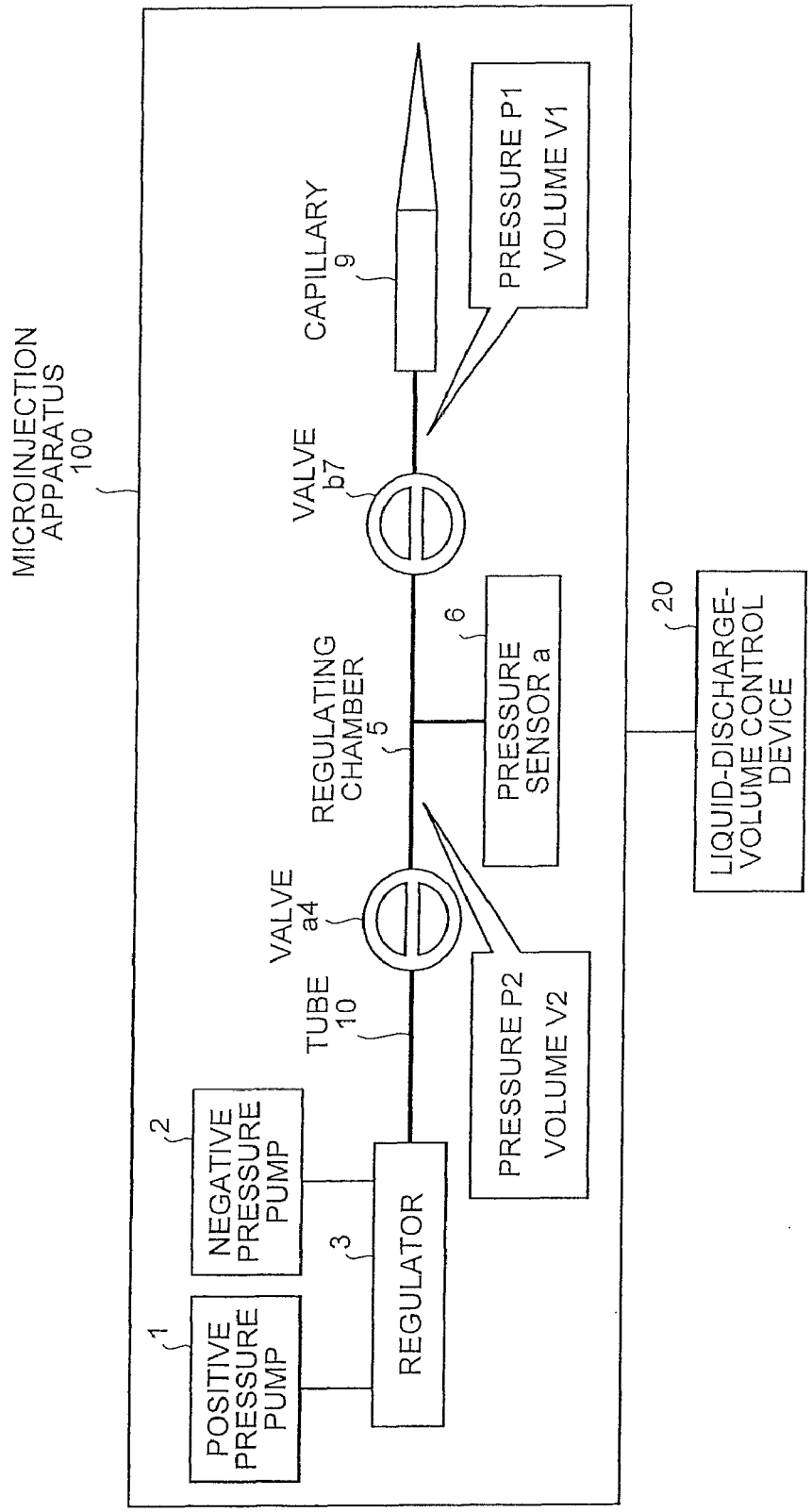
FIG. 1 is a schematic of a microinjection apparatus according to a first embodiment of the present invention.
Figure 2A:
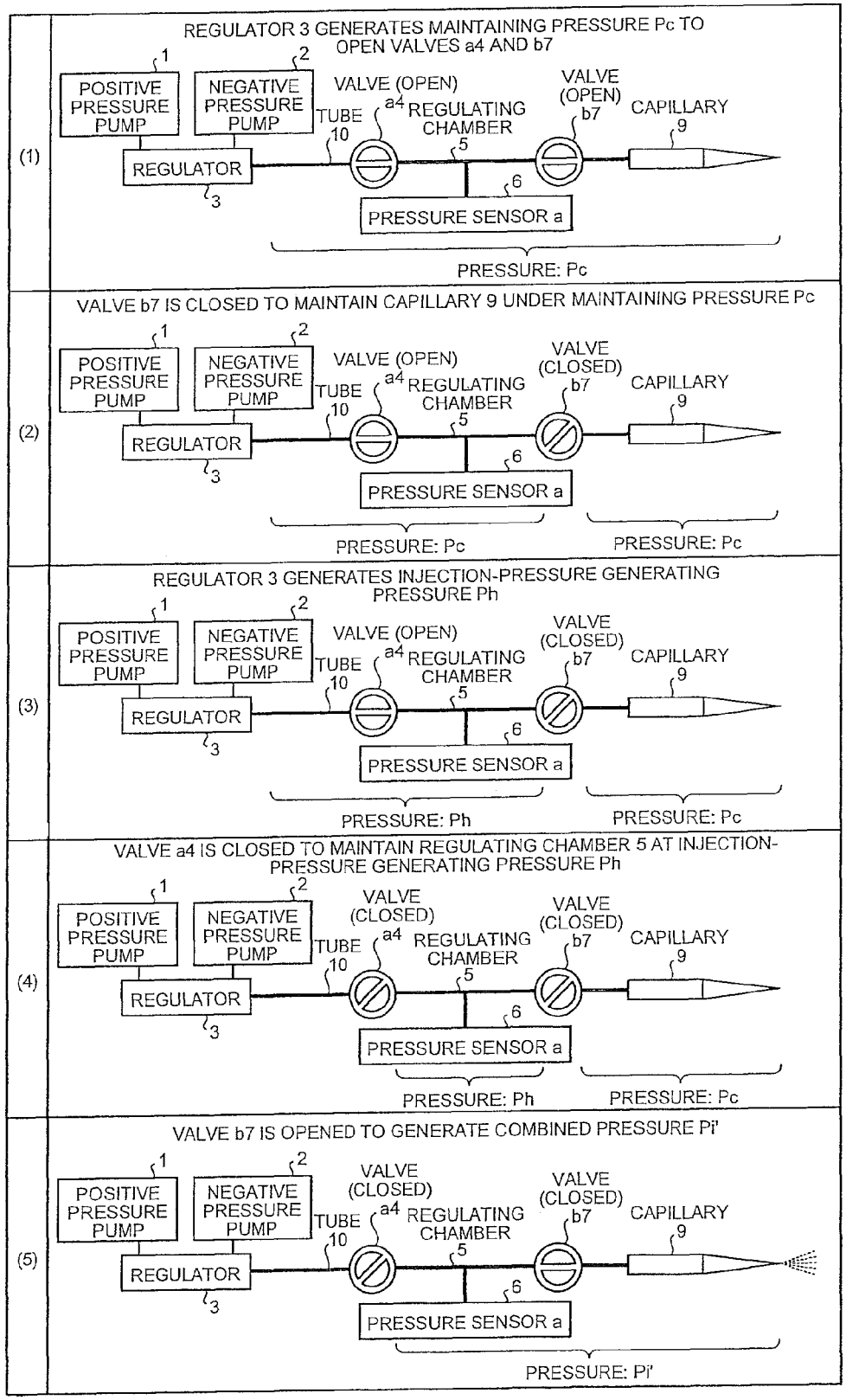
Figure 2B:
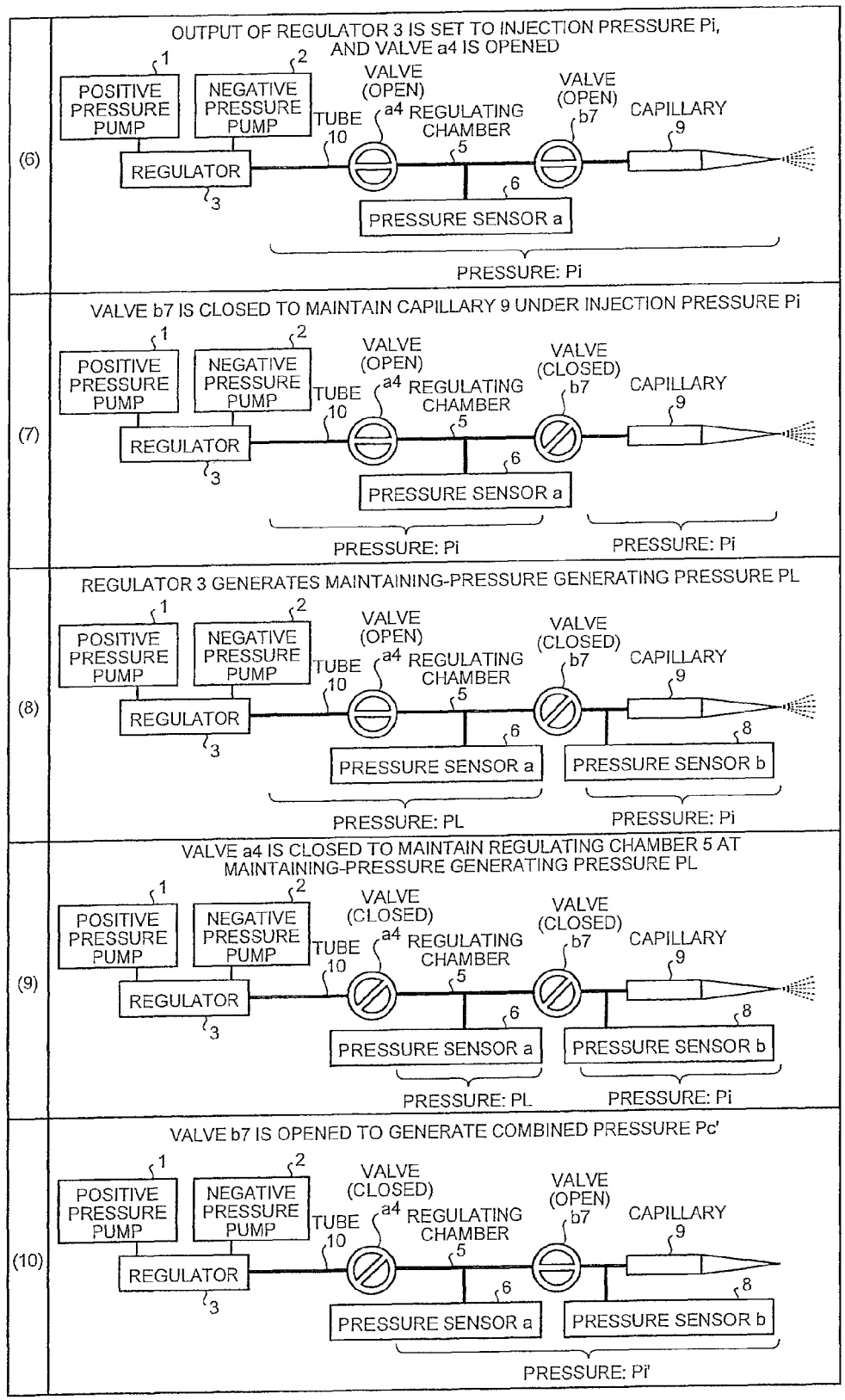

FIG. 1 is a schematic of a microinjection apparatus 100 according to a first embodiment of the present invention. FIGS. 2A to 2C are schematics for explaining an overview and features of a liquid discharge volume control method according to the first embodiment.

The microinjection apparatus 100, which is connected to the positive pressure pump 1 and the negative pressure pump 2, includes the regulator 3, the regulating chamber 5, the capillary 9, the valve a4, the valve b7, and the pressure sensor a6. The regulator 3 maintains a pressure developed by the pumps 1 and 2 constant. The regulating chamber 5 traps the pressure maintained by the regulator 3. The capillary 9 is filled with a solution. The valve a4 is between the regulator 3 and the regulating chamber 5. The valve b7 is between the regulating chamber 5 and the capillary 9. The pressure sensor a6 detects a pressure in the regulating chamber 5. The regulator 3, the valve a4, the regulating chamber 5, the pressure sensor a6, the valve b7, and the capillary 9 are connected by the tube 10 (indicated by thick lines). The regulating chamber 5 referred to here is a portion of the tube 10 that connects between the valve a4 and the pressure sensor a6 and between the pressure sensor a6 and the valve b7. The liquid-discharge-volume control device 20 controls operations of the microinjection apparatus 100. For example, as each of the valves a4 and b7, a valve including an electromagnetic solenoid is employed. The liquid-discharge-volume control device 20 generates an electric signal, thereby controlling opening and closing operations of each of the valves a4 and b7.

While the liquid-discharge-volume control device 20 of the first embodiment is capable of controlling a liquid volume accurately as in the conventional technology, the salient feature of the liquid-discharge-volume control device 20 is to provide more accurate and stable control of a liquid discharge volume.

The salient feature is briefly explained. First, the liquid-discharge-volume control device 20 of the first embodiment performs motion control of the microinjection apparatus 100 as shown in FIG. 2A to apply the injection pressure Pi to the capillary 9 to start discharge of liquid. Specifically, the liquid-discharge-volume control device 20 causes the regulator 3 to generate the maintaining pressure Pc by using the positive pressure pump 1 and the negative pressure pump 2, and then opens the valves a4 and b7 (see (1) of FIG. 2A). Next, an operator connects the capillary 9 filled with a solution to the tube 10. Hence, the liquid filled in the capillary 9 is retained in the capillary 9 without flowing backward. The state shown in (1) of FIG. 2A is maintained until penetration of a cell with the capillary 9 by the operator under a microscope to discharge (to inject) the liquid becomes ready.

When penetration of the cell with the capillary 9 by the operator to start injection becomes available, as shown in (2) of FIG. 2A, the liquid-discharge-volume control device 20 closes the valve b7 to maintain the capillary 9 under the maintaining pressure Pc in accordance with an operator request to start injection, and causes the regulator 3 to generate the injection-pressure generating pressure Ph (described later), which is a pressure necessary to generate the injection pressure Pi, by using the positive pressure pump 1 and the negative pressure pump 2 (see (3) of FIG. 2A).

As shown in (4) of FIG. 2A, the liquid-discharge-volume control device 20 closes the valve a4 to maintain the regulating chamber 5 under the injection-pressure generating pressure Ph, and then opens the valve b7. Consequently, the injection-pressure generating pressure Ph and the maintaining pressure Pc are combined into a combined pressure Pi', and liquid is discharged out of the capillary 9 (see (5) of FIG. 2A). As explained above, instantaneous opening/closing of the valves a4 and b7 causes the pressure applied to the capillary to change from the maintaining pressure to the injection pressure quickly. The series of operations are also disclosed in Japanese Patent Application Laid-Open No. 2006-133512, "METHOD FOR DISCHARGING LIQUID INTO CELL AND MICROINJECTION APPARATUS" by the inventor of this application.

However, a change in the "volume ratio η" caused by elements such as flexibility of the material of the tube 10, pressure values, and a pressure-applying time can develop a slight error in the obtained combined pressure Pi' in relation to the injection pressure Pi.

Therefore, as shown in (6) of FIG. 2B, the liquid-discharge-volume control device 20 of the first embodiment sets an output of the regulator 3 to the injection pressure Pi, thereby reapplying the injection pressure Pi to the capillary 9. This corrects the error included in the combined pressure Pi', which is obtained at step (5) of FIG. 2A, in relation to the injection pressure Pi.

Subsequently, as shown in (7) of FIG. 2B, the liquid-discharge-volume control device 20 of the first embodiment closes the valve b7 to maintain the capillary 9 under the injection pressure Pi, and causes the regulator 3 to generate the maintaining-pressure generating pressure PL (described later), which is necessary to generate the maintaining pressure Pc (see (8) of FIG. 2B).

As shown in (9) of FIG. 2B, the liquid-discharge-volume control device 20 closes the valve a4 to maintain the regulating chamber 5 under the maintaining-pressure generating pressure PL, and then opens the valve b7 (see (10) of FIG. 2B). Consequently, the maintaining-pressure generating pressure PL and the injection pressure Pi are combined into the combined pressure Pc', which terminates the discharge of liquid out of the capillary 9. As explained above, instantaneous opening/closing of the valves a4 and b7 causes the pressure applied to the capillary to change from the injection pressure to the maintaining pressure quickly. Accordingly, an injection pressure that takes a rectangular waveform can be applied to the capillary 9, which allows to perform accurate control of a liquid discharge volume by adjusting the injection pressure and an injection-pressure application time (a period of time required to process steps (5) of FIG. 2A to (10) of FIG. 2B). Meanwhile, as in the case of the combined pressure Pi', the combined pressure Pc' can have a slight error in relation to the maintaining pressure Pc.

When the liquid-discharge-volume control device 20 is required to consecutively discharge liquid to another cell, the liquid-discharge-volume control device 20 causes the regulator 3 to generate the maintaining pressure Pc, and opens the valve a4 to shift the state from that shown in (10) of FIG. 2B to that shown in (1) of FIG. 2A, to perform operation control including the same steps as above. Shifting from step (10) of FIG. 2B to step (1) of FIG. 2A causes the process to enter standby mode until a start of a next injection cycle, and corrects the error, which can be included in the combined pressure Pc' obtained at step (10) of FIG. 2B, in relation to the maintaining pressure Pc. Therefore, this operation achieves reapplication of the maintaining pressure to the capillary 9 even when the process is not followed by another injection.

FIG. 2C is a graph that depicts open/close state of the valves a4 and b7, pressure output from the regulator 3, pressure applied to the regulating chamber 5, and pressure applied to the capillary 9 in (1) to (5) of FIG. 2A and (6) to (9) of FIG. 2B together. The numbers 1 to 10 (STEP) on the horizontal axis correspond to steps (1) to (10) of FIGS. 2A and 2B, respectively.

Therefore, even when an injection pressure or a maintaining pressure obtained as above involves an error, the liquid discharge volume control method of the first embodiment can absorb the error by reapplying the injection pressure or the maintaining pressure to the capillary 9. Hence, as previously explained as the salient feature, the method achieves more accurate and stable control of a liquid discharge volume.

Meanwhile, in contrast to the microinjection apparatus 1000, the microinjection apparatus 100 does not include the pressure sensor b8. This is because, since a pressure value detected by the pressure sensor a6 with the valve b7 opened is identical with a pressure value (pressure on the capillary side) detected by the pressure sensor b8 at the same point in time, a pressure value detected by the pressure sensor a6 immediately before the valve b7 is closed is employed as the capillary-side pressure so that the pressure sensor a6 functions also as the pressure sensor b8.

The above-mentioned injection-pressure generating pressure Ph for generating the injection pressure Pi and the maintaining-pressure generating pressure PL for generating the maintaining pressure Pc are explained. A relation between the pressure at a point in time before the valve b7 is opened and the pressure at a point in time after the valve b7 is opened can be obtained using an equation of state of gas. As shown in FIG. 1, the gas volume on the capillary 9 side is denoted as V1, the pressure on the capillary 9 side at a point in time before the valve b7 is opened as P1, the gas volume of the regulating chamber 5 as V2, and the pressure in the regulating chamber 5 at a point in time before the valve b7 is opened as P2. In this case, relations between the pressure P, which is a pressure at a point in time after the valve b7 is opened, and the volume ratio η ($\eta = V2/V1$) are expressed in each of equations (1) and (2) of FIG. 13. Accordingly, the pressure P2 that need to be retained in the regulating chamber 5 before the valve b7 is opened to generate the pressure P after the valve b7 is opened can be expressed by equation (3) of FIG. 13.

Meanwhile, the pressure P1 on the capillary 9 side between closing and opening of the valve b7 can be obtained as a pressure value detected by the pressure sensor a6 immediately before the valve b7 is closed; the pressure P2 of the regulating chamber 5 at a point in time before the valve b7 is opened can be obtained using the pressure sensor a6; and the pressure P at a point in time after the valve b7 is opened can be obtained using the pressure sensor a6. Therefore, the volume ratio η can be obtained in advance from equation (2) of FIG. 13 using the pressure values determined by performing a preliminary discharge of liquid.

The injection-pressure generating pressure Ph or the maintaining-pressure generating pressure PL is calculated using the volume ratio η and equation (3) of FIG. 13. The injection-pressure generating pressure Ph is calculated by substituting the injection pressure Pi for the pressure P, which is the pressure at a point in time after the valve b7 is opened, and the maintaining pressure Pc for the pressure P1, which is the pressure on the capillary 9 side at a point in time before the valve b7 is opened, in equation (3) of FIG. 13. The maintaining-pressure generating pressure PL is calculated by substituting the maintaining pressure Pc for the pressure P, which is the pressure at a point in time after the valve b7 is opened, and the injection pressure Pi for the pressure P1, which is the pressure on the capillary 9 side at a point in time before the valve b7 is opened, in equation (3) of FIG. 13.

Figure 3:
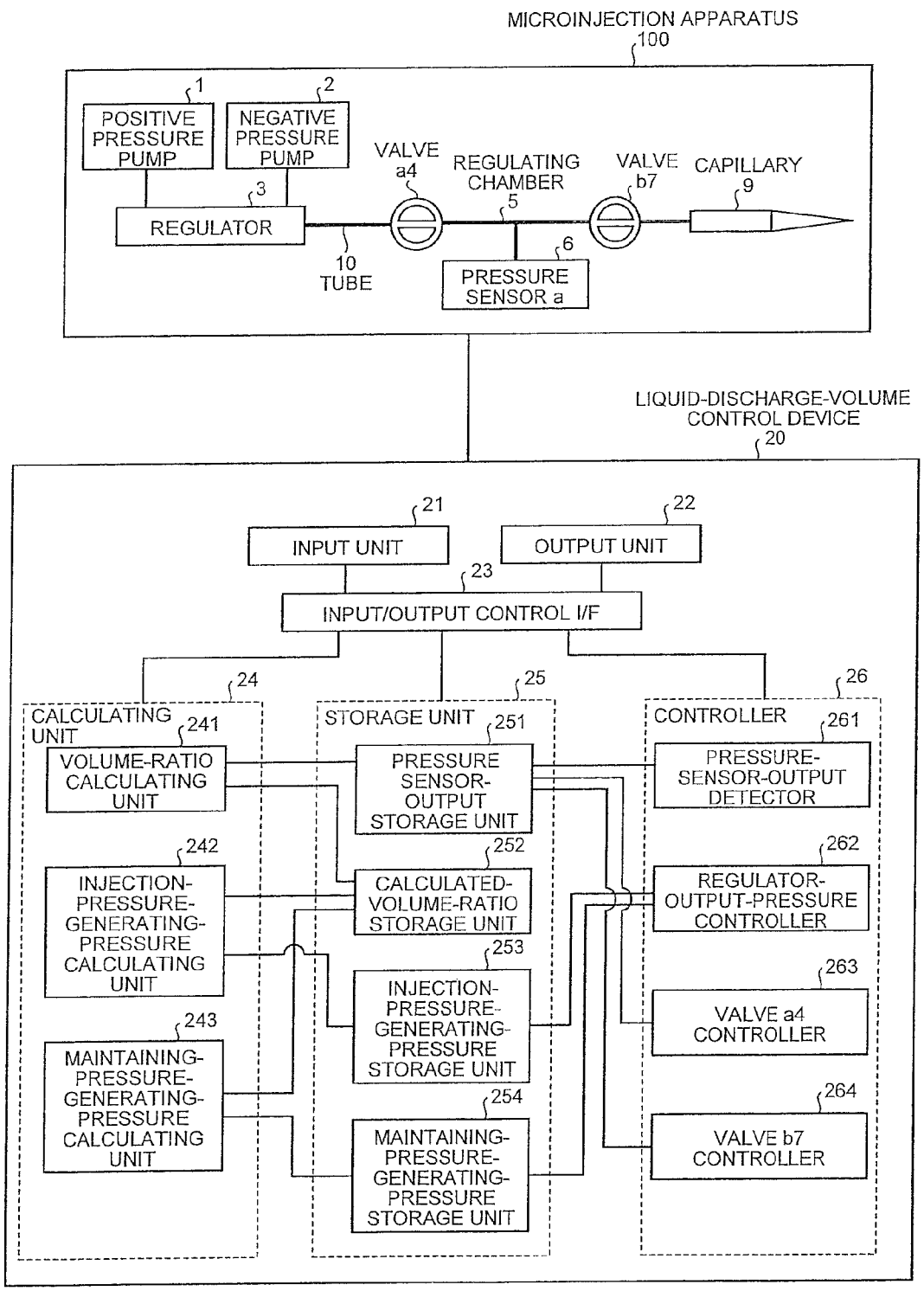
FIG. 3 is a block diagram of the liquid discharge volume control device shown in FIG. 1.

FIG. 3 is a block diagram of the liquid discharge volume control device 20 according to the first embodiment. The liquid-discharge-volume control device 20 includes an input unit 21, an output unit 22, an input/output control interface (I/F) 23, a calculating unit 24, a storage unit 25, and a controller 26, and is connected to the microinjection apparatus 100.

The input unit 21 includes a keyboard, a mouse, and the like, and receives an operator input on various conditions (e.g., a liquid discharge volume to be set based on the injection pressure Pi and a pressure-application time, and the maintaining pressure Pc to be set based on the viscosity of a liquid filled in the capillary 9, and the like) pertaining to injection, and an operator request to start injection.

The output unit 22 outputs a control instruction issued by the controller 26, described later, to the microinjection apparatus 100, and controls operations of the microinjection apparatus 100.

The input/output control I/F 23 controls data transfer to and from the input unit 21, the output unit 22, the calculating unit 24, the storage unit 25, and the controller 26.

The storage unit 25 stores therein data to be used in various processes performed by the calculating unit 24, results of the various processes performed by the calculating unit 24, and records of various control operations performed by the controller 26. The storage unit 25 includes a pressure sensor-output storage unit 251, a calculated-volume-ratio storage unit 252, an injection-pressure-generating-pressure storage unit 253, and a maintaining-pressure-generating-pressure storage unit 254.

The pressure sensor-output storage unit 251 stores therein, in addition to a pressure value obtained from the pressure sensor a6 through a pressure sensor-output detector 261, described later, a record of opening/closing control on the valve a4 performed by a valve a4 controller 263, described later, and a record of opening/closing control on the valve b7 performed by a valve b7 controller 264, described later.

The calculated-volume-ratio storage unit 252 stores therein a volume ratio calculated by a volume-ratio calculating unit 241, described later. The injection-pressure-generating-pressure storage unit 253 stores therein an injection-pressure generating pressure calculated by an injection-pressure-generating-pressure calculating unit 242, described later. The maintaining-pressure-generating-pressure storage unit 254 stores therein a maintaining-pressure generating pressure calculated by a maintaining-pressure-generating-pressure calculating unit 243, described later. The respective units are described in detail later.

The controller 26 performs various control operations in accordance with an operator request transmitted from the input/output control I/F 23. The controller 26 includes the pressure sensor-output detector 261, a regulator-output-pressure controller 262, the valve a4 controller 263, and the valve b7 controller 264.

The pressure sensor-output detector 261 obtains a pressure value detected by the pressure sensor a6 from the pressure sensor a6, and stores therein the result in the pressure sensor-output storage unit 251.

The regulator-output-pressure controller 262 causes the regulator 3 to generate a pressure of a predetermined magnitude by using the positive pressure pump 1 and the negative pressure pump 2. Put another way, the regulator-output-pressure controller 262 causes the regulator 3 to generate the injection pressure Pi or the maintaining pressure Pc, which is a setting condition input to the input unit 21, the injection-pressure generating pressure Ph stored in the injection-pressure-generating-pressure storage unit 253, or the maintaining-pressure generating pressure PL stored in the maintaining-pressure-generating-pressure storage unit 254.

The valve a4 controller 263 controls opening and closing operations of the valve a4. Specifically, the valve a4 controller 263 controls the series of opening and closing operations of the valve a4 shown in FIGS. 2A and 2B by using, e.g., electric signals. The valve a4 controller 263 also transmits a record of opening/closing control on the valve a4 to the pressure sensor-output storage unit 251. The pressure sensor-output storage unit 251 stores therein the record of opening/closing control on the valve a4.

The valve b7 controller 264 controls opening closing operations of the valve b7. The valve b7 controller 264 also transmits a record of opening/closing control on the valve b7 to the pressure sensor-output storage unit 251. The pressure sensor-output storage unit 251 stores therein the record of opening/closing control on the valve b7.

The calculating unit 24 performs various processes in accordance with an operator request transmitted from the input/output control I/F 23. The calculating unit 24 includes the volume-ratio calculating unit 241, the injection-pressure-generating-pressure calculating unit 242, and the maintaining-pressure-generating-pressure calculating unit 243.

The volume-ratio calculating unit 241 calculates the volume ration from a record on an output pressure value, which is detected by the pressure sensor a6 and stored in the pressure sensor-output storage unit 251, a control record of the valve a4 controller 263, and a control record of the valve b7 controller 264, and stores the calculation result in the calculated-volume-ratio storage unit 252.

Calculation of a volume ratio is explained in detail. The valve a4 controller 263 opens the valve a4, the valve b7 controller 264 opens the valve b7, and the regulator-output-pressure controller 262 causes the regulator 3 to generate an appropriate pressure P1. The valve b7 controller 264 then closes the valve b7 to maintain the capillary 9 under the pressure P1. As the value of the pressure P1, a pressure value detected by the pressure sensor a6 immediately before the valve b7 is closed is employed by referring to the control record of the valve b7 controller 264. The regulator-output-pressure controller 262 causes the regulator 3 to generate an appropriate pressure P2, and the valve a4 controller 263 closes the valve a4 to maintain the regulating chamber 5 under the pressure P2. As the value of the pressure P2, a value detected by the pressure sensor a6 at this stage is employed by referring to the control record of the valve a4 controller 263 and the control record of the valve b7 controller 264. Subsequently, the valve b7 controller 264 opens the valve b7 to combine the pressure P1 with the pressure P2 to generate a new pressure P. The pressure P is applied to the capillary 9. As the value of the pressure P, a value detected by the pressure sensor a6 at this stage is employed by referring to the control record of the valve a4 controller 263 and the control record of the valve b7 controller 264. The volume ratio $\eta$ is obtained from the actual values of P1, P2, and P by using equation (2) of FIG. 13.

The injection-pressure-generating-pressure calculating unit 242 calculates the injection-pressure generating pressure Ph, which is necessary to obtain the injection pressure Pi in combination with the maintaining pressure Pc, by using the volume ratio $\eta$ stored in the calculated-volume-ratio storage unit 252, and stores the calculation result in the injection-pressure-generating-pressure storage unit 253. Specifically, injection-pressure-generating-pressure calculating unit 242 uses the volume ratio $\eta$ to calculate the injection-pressure generating pressure Ph, and substitutes the injection pressure Pi for the pressure P, which is the pressure at a point in time after the valve b7 is opened, and the maintaining pressure Pc for the pressure P1, which is the pressure on the capillary 9 side at a point in time before the valve b7 is opened, in equation (3) of FIG. 13. Thus, the following equation is formed:

$$Ph = ((\eta+1)Pi\cdot Pc)/\eta.$$

The maintaining-pressure-generating-pressure calculating unit 243 calculates the maintaining-pressure generating pressure PL, which is necessary to generate the maintaining pressure Pc in combination with the injection pressure Pi, by using the volume ratio η stored in the calculated-volume-ratio storage unit 252, and stores the calculation result in the maintaining-pressure-generating-pressure storage unit 254. Specifically, the maintaining-pressure-generating-pressure calculating unit 243 calculates the maintaining-pressure generating pressure PL by substituting the maintaining pressure Pc for the pressure P, which is the pressure at a point in time after the valve b7 is opened, and the injection pressure Pi for the pressure P1, which is the pressure on the capillary 9 side at a point in time before the valve b7 is opened, in equation (3) of FIG. 13. Thus, the following equation is formed:

$$Ph = ((\eta+1)Pc - Pi)/\eta.$$

Figure 4:
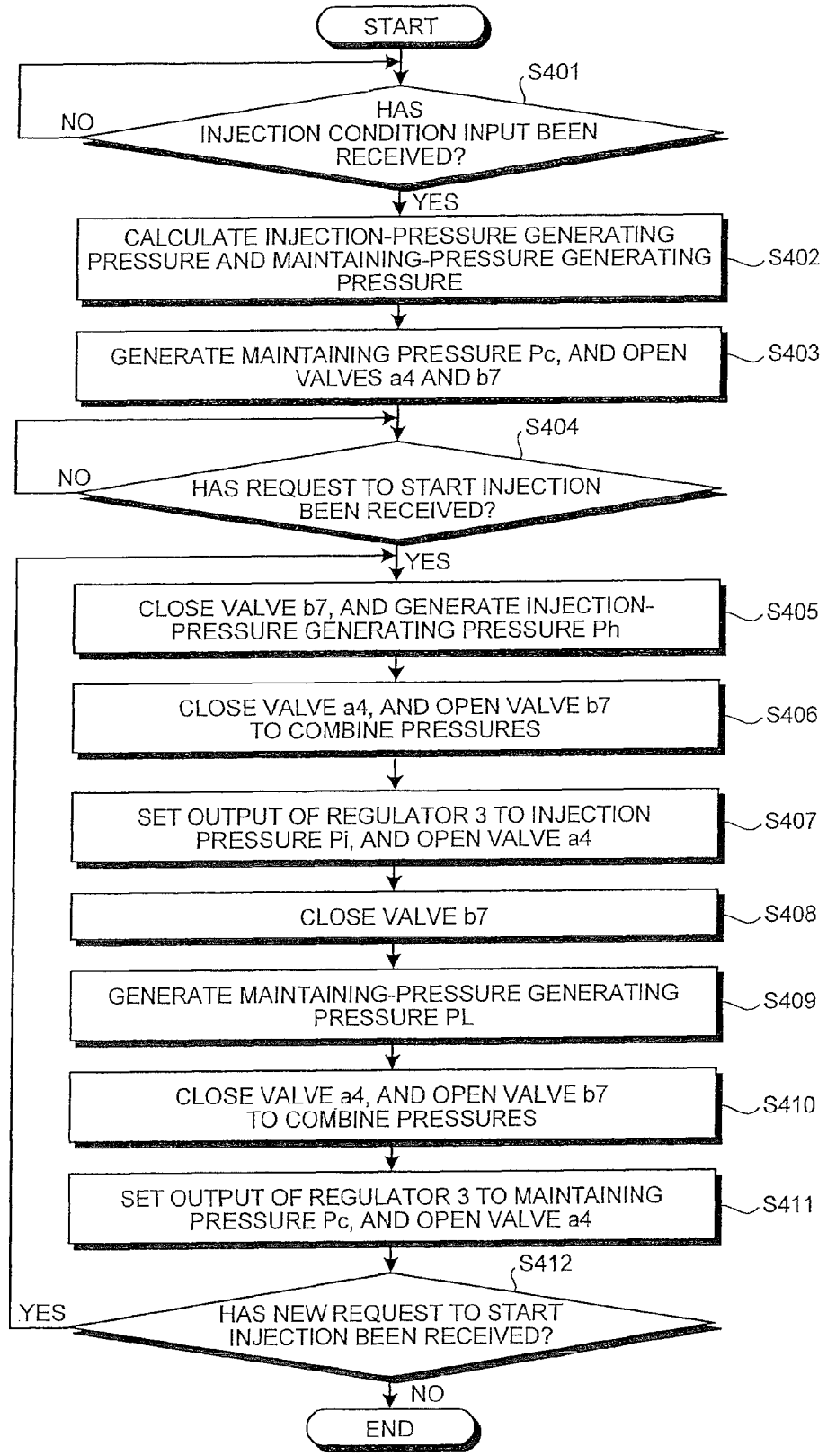
FIG. 4 is flowchart of a process performed by the liquid discharge volume control device shown in FIG. 1.

FIG. 4 is a flowchart of a process procedure performed by the liquid discharge volume control device 20.

First, when the liquid-discharge-volume control device 20 receives a new operator input on various conditions (e.g., a liquid discharge volume to be set based on the injection pressure Pi and a pressure-application time, and the maintaining pressure Pc to be set based on the viscosity of a liquid filled in the capillary 9, and the like) pertaining to injection via the keyboard or the mouse (YES at step S401), the injection-pressure-generating-pressure calculating unit 242 and the maintaining-pressure-generating-pressure calculating unit 243 calculate the injection-pressure generating pressure Ph and the maintaining-pressure generating pressure PL, respectively (step S402).

While the regulator-output-pressure controller 262 causes the regulator 3 to generate the maintaining pressure Pc by using the positive pressure pump 1 and the negative pressure pump 2, the valve a4 controller 263 opens the valve a4, and the valve b7 controller 264 opens the valve b7 (step S403). Hence, the liquid filled in the capillary 9 is prevented from flowing backward into the capillary 9.

Thereafter, the liquid-discharge-volume control device 20 maintains the state until when penetration of a cell with the capillary 9 by the operator to start injection becomes available and the liquid-discharge-volume control device 20 receives an operator request to start injection (NO at step S404).

On the other hand, when penetration of a cell with the capillary 9 by the operator to start injection becomes available and the liquid-discharge-volume control device 20 receives an operator request to start injection (YES at step S404), the valve b7 controller 264 closes the valves b7, and the regulator-output-pressure controller 262 causes the regulator 3 to generate the injection-pressure generating pressure Ph by using the positive pressure pump 1 and the negative pressure pump 2 (step S405).

While the valve a4 controller 263 closes the valve a4 to maintain the regulating chamber 5 under the injection-pressure generating pressure Ph, the valve b7 controller 264 opens the valve b7 to combine the injection-pressure generating pressure Ph with the maintaining pressure Pc. The newly-generated combined pressure is applied to the capillary 9 (step S406). Consequently, the pressure applied to the capillary 9 increases quickly to start discharging of liquid out of the capillary 9.

Subsequently, while the regulator-output-pressure controller 262 causes the regulator 3 to generate the injection pressure Pi by using the positive pressure pump 1 and the negative pressure pump 2, the valve a4 controller 263 opens the valve a4 (step S407). This operation allows, even when the combined pressure obtained at step S406 involves an error in relation to the injection pressure Pi, to correct the error, and to apply the injection pressure Pi to the capillary 9.

While the valve b7 controller 264 closes the valves b7 (step S408), thereby maintaining the capillary 9 under the injection pressure Pi, the regulator-output-pressure controller 262 causes the regulator 3 to generate the maintaining-pressure generating pressure PL by using the positive pressure pump 1 and the negative pressure pump 2 (step S409).

While the valve a4 controller 263 closes the valve a4 to maintain the regulating chamber 5 under the maintaining-pressure generating pressure PL, the valve b7 controller 264 opens the valve b7 to combine the maintaining-pressure generating pressure PL with the injection pressure Pi. The newly-generated combined pressure is applied to the capillary 9 (step S410). Consequently, the pressure applied to the capillary 9 decreases quickly to terminate the discharge of liquid out of the capillary 9.

While the regulator-output-pressure controller 262 causes the regulator 3 to generate the maintaining pressure Pc by using the positive pressure pump 1 and the negative pressure pump 2, the valve a4 controller 263 opens the valve a4 (step S411). This operation allows, even when the combined pressure obtained at step S410 involves an error in relation to the maintaining pressure Pc, to correct the error, and to apply the maintaining pressure Pc to the capillary 9.

Upon receipt of a new operator request to start injection (YES at step S412), the liquid-discharge-volume control device 20 performs the process pertaining to step S405 and subsequent steps. When a new request for injection start is not issued (NO at step S412), the process ends.

As explained above, according to the first embodiment, opening the valve b7 in the state where the valves a4 and b7 are closed causes an injection-pressure generating pressure trapped between the valves a4 and b7 and a maintaining pressure applied to the capillary 9 to be combined into an injection pressure. Hence, discharge of the liquid out of the capillary 9 is started by the injection pressure. Thereafter, while an output pressure of the regulator 3 is set to the injection pressure, the valve a4 is opened to apply the injection pressure to the capillary 9, and then the valve b7 is opened in a state where the valves a4 and b7 are closed. Accordingly, a maintaining-pressure generating pressure trapped between the valves a4 and b7 and the injection pressure applied to the capillary 9 are combined into a maintaining pressure. Hence, the discharge of liquid is terminated by the maintaining pressure. Thereafter, while the output pressure of the regulator 3 is set to the maintaining pressure, the valve a4 is opened to apply the maintaining pressure to the capillary 9. Therefore, even when, for example, the injection pressure or the maintaining pressure generated as above involves an error, the error can be absorbed by reapplying the injection pressure or the maintaining pressure to the capillary 9, thereby achieving more accurate and stable control of a liquid discharge volume.

According to the first embodiment, calculation of a volume ratio is performed by employing, as an actual value of the pressure applied to the capillary 9, a value detected by the pressure sensor a6 immediately before the valve b7 is closed, and employing, as a value of the combined pressure generated when the valve b7 is opened, a value detected by the pressure sensor a6. Therefore, the magnitude of the pressure output to the capillary can be detected without provision of another pressure sensor for detecting the pressure, thereby suppressing a cost of capital investment.

In the first embodiment, the injection-pressure generating pressure Ph or the maintaining-pressure generating pressure PL is calculated based on a previously-calculated volume ratio. In a second embodiment of the present invention, a volume ratio to be borne under a pressure condition defined by input is recalculated to calculate the injection-pressure generating pressure Ph or the maintaining-pressure generating pressure PL.

Figure 5:
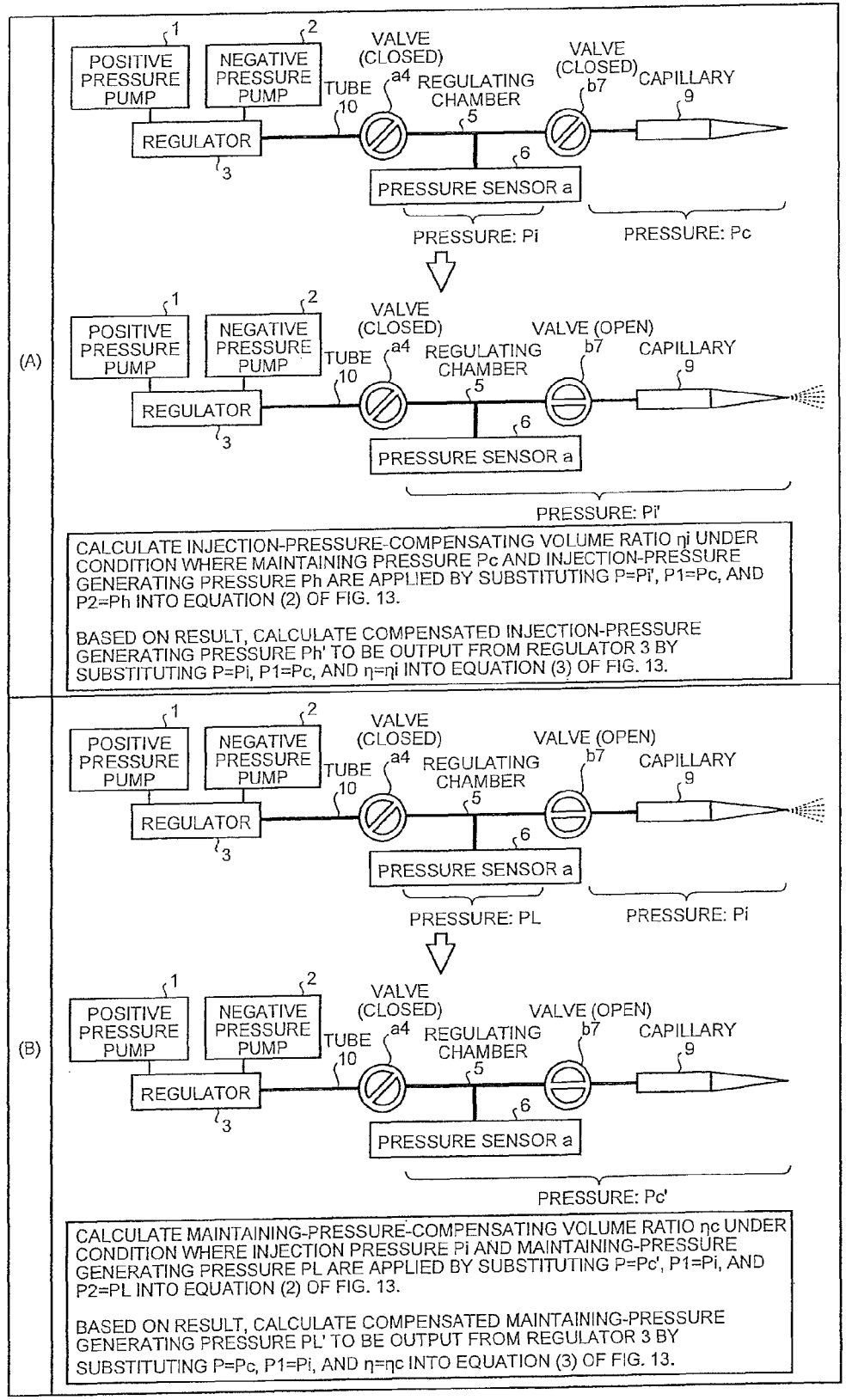
FIG. 5 is a schematic for explaining an overview and features of a liquid discharge volume control device according to a second embodiment.

FIG. 5 is a schematic for explaining an overview and features of the liquid discharge volume control device of the second embodiment.

As in the first embodiment, the liquid discharge volume control device of the second embodiment calculates the injection-pressure generating pressure Ph and the maintaining-pressure generating pressure PL from the injection pressure Pi and the maintaining pressure Pc, which are input by an operator, using the already-calculated volume ratio η and equation (3) of FIG. 13.

The liquid discharge volume control device of the second embodiment controls operations of the microinjection apparatus 100 to open the valve b7 in a state where the injection-pressure generating pressure Ph is maintained in the regulating chamber 5 and the capillary 9 receives the maintaining pressure Pc as shown in the upper diagram in (A) of FIG. 5, thereby generating a combined pressure as shown in the lower diagram in (A) of FIG. 5. At this timing, an actual value of the injection-pressure generating pressure Ph, that of the maintaining pressure Pc, and a value of the combined pressure Pi' are obtained using the pressure sensor a6. As the actual value of the maintaining pressure Pc, a value detected by the pressure sensor a6 immediately before closing of the valve b7 causes the state to shift to that shown in the upper diagram in (A) of FIG. 5 is employed.

Subsequently, the liquid discharge volume control device of the second embodiment calculates an injection-pressure-compensating volume ratio ηi, which is a volume ratio to be borne under a condition where the tube 10 receives the maintaining pressure Pc and the injection-pressure generating pressure Ph, by using equation (2) of FIG. 13. Specifically, the actual value Pi' is substituted for P, an actual value of the maintaining pressure Pc is substituted for P1, and an actual value of the injection-pressure generating pressure Ph is substituted for P2 in equation (2) of FIG. 13. Thus, the following equation is formed:

$$\eta i = ((Pc-Pi')/(Pi-Ph))$$

where Pc and Ph are actual values. A compensated injection-pressure generating pressure Ph', which is necessary to generate a renewed injection pressure Pi, is calculated using the injection-pressure-compensating volume ratio ηi. Specifically, with equation (3) of FIG. 13, the compensated injection-pressure generating pressure Ph' is calculated by substituting Pi, which is a pressure value of an operator input, for P, the maintaining pressure Pc for P1, and the injection-pressure-compensating volume ratio ηi for the volume ratio η, i.e., Ph'=((ηi+1)(Pi−Pc)/ηi.

The liquid discharge volume control device of the second embodiment controls operations of the microinjection apparatus 100 to open the valve b7 in a state where the maintaining-pressure generating pressure PL is maintained in the regulating chamber 5 and the capillary 9 receives the injection pressure Pi as shown in the upper diagram in (B) of FIG. 5, thereby obtaining a combined pressure as shown in the lower diagram in (B) of FIG. 5. At this timing, an actual value of the maintaining-pressure generating pressure PL, that of the injection pressure Pi, and a value of the combined pressure Pi' are obtained using the pressure sensor a6. As the actual value of the injection pressure Pi, a value detected by the pressure sensor a6 immediately before closing of the valve b7 causes the state to shift to that shown in the upper diagram in (B) of FIG. 5 is employed.

Subsequently, the liquid discharge volume control device of the second embodiment calculates a maintaining-pressure-compensating volume ratio ηc, which is a volume ratio to be borne under a condition where the tube 10 receives the injection pressure Pi and the maintaining-pressure generating pressure PL, by using equation (2) of FIG. 13. Specifically, the actual value Pc' is substituted for P, an actual value of the injection pressure Pi is substituted for P1, and an actual value of the maintaining-pressure generating pressure PL is substituted for P2 in equation (2) of FIG. 13. Thus, the following equation is formed:

$$\eta i = ((Pi-Pc')/(Pc'-PL))$$

where Pi and PL are actual values.

A compensated maintaining-pressure generating pressure PL', which is necessary to generate a renewed maintaining pressure Pc, is calculated using the maintaining-pressure-compensating volume ratio ηc. Specifically, with equation (3) of FIG. 13, the compensated maintaining-pressure generating pressure PL' is calculated by substituting Pc, which is a pressure value of an operator input, for P, the injection pressure Pi for P1, and the maintaining-pressure-compensating volume ratio ηc for the volume ratio η, i.e., PL'=((ηc+1)Pc−Pi)/η.

The liquid discharge volume control device of the second embodiment performs discharge of liquid into a cell by using the compensated injection-pressure generating pressure Ph' and the compensated maintaining-pressure generating pressure PL' in accordance with an operator request to start injection.

In this embodiment, the compensated injection-pressure generating pressure Ph' and the compensated maintaining-pressure generating pressure PL' are calculated based on an actual combined pressure value, and the like, obtained through a single series of operations. However, alternatively, the compensated injection-pressure generating pressure Ph' and the compensated maintaining-pressure generating pressure PL' can be calculated based on an average combined pressure value obtained by repeating the series of operations shown in (A) and (B) of FIG. 5 a plurality of times.

As explained above, the liquid discharge volume control device of the second embodiment is capable of recalculating a magnitude of pressure to be output from the regulator to generate an injection pressure or a maintaining pressure while compensating a volume ratio based on an actual pressure value taken for each injection setting condition. Accordingly, stabilization of liquid discharge volume is achieved under any setting condition.

Next, the liquid discharge volume control device according to the second embodiment is explained with reference to FIG. 3. The liquid discharge volume control device 20 according to the second embodiment is basically similar to that of the first embodiment except that the volume-ratio calculating unit 241, the injection-pressure-generating-pressure calculating unit 242, and the maintaining-pressure-generating-pressure calculating unit 243 operate differently from those in the first embodiment. Therefore, the same explanation is not repeated.

The volume-ratio calculating unit 241 recalculates the injection-pressure-compensating volume ratio ηi and the injection-pressure-compensating volume ratio ηc, and stores the calculation results in the calculated-volume-ratio storage unit 252. That is, the volume-ratio calculating unit 241 calculates the injection-pressure-compensating volume ratio $\eta i$, which is a volume ratio to be borne under a condition where the tube 10 receives the maintaining pressure Pc and the injection-pressure generating pressure Ph, based on the actual pressure value detected in the step shown in (A) of FIG. 5 and stored in the pressure sensor-output storage unit 251 by using equation (2) of FIG. 13, and stores the calculation result in the calculated-volume-ratio storage unit 252. Specifically, the injection-pressure-compensating volume ratio $\eta i$ is calculated by substituting the actual value Pi' for P, an actual value of the maintaining pressure Pc for P1, and an actual value of the injection-pressure generating pressure Ph for P2 in equation (2) of FIG. 13.

The volume-ratio calculating unit 241 calculates the maintaining-pressure-compensating volume ratio $\eta c$, which is a volume ratio to be borne under a condition where the tube 10 receives the maintaining-pressure generating pressure PL and the injection pressure Pi, based on the actual pressure value detected in the step shown in (B) of FIG. 5 and stored in the pressure sensor-output storage unit 251 by using equation (2) of FIG. 13, and stores the calculation result in the calculated-volume-ratio storage unit 252. Specifically, the maintaining-pressure-compensating volume ratio $\eta c$ is calculated by substituting the actual value Pi' for P, an actual value of the injection pressure Pc for P1, and an actual value of the maintaining-pressure generating pressure PL for P2 in equation (2) of FIG. 13.

The injection-pressure-generating-pressure calculating unit 242 calculates the compensated injection-pressure generating pressure Ph', which is necessary to generate a renewed injection pressure Pi, using the injection-pressure-compensating volume ratio $\eta i$ stored in the calculated-volume-ratio storage unit 252. Specifically, with equation (3) of FIG. 13, the compensated injection-pressure generating pressure Ph' is calculated by substituting Pi, which is a pressure value of an operator input, for P, the maintaining pressure Pc for P1, and the injection-pressure-compensating volume ratio $\eta i$ for the volume ratio $\eta$.

The maintaining-pressure-generating-pressure calculating unit 243 calculates the compensated maintaining-pressure generating pressure PL', which is necessary to generate a renewed maintaining pressure Pc, using the maintaining-pressure-compensating volume ratio $\eta c$ stored in the calculated-volume-ratio storage unit 252. Specifically, with equation (3) of FIG. 13, the compensated maintaining-pressure generating pressure PL' is calculated by substituting Pc, which is a pressure value of an operator input, for P, the injection pressure Pi for P1, and the maintaining-pressure-compensating volume ratio $\eta c$ for the volume ratio $\eta$.

Figure 6:
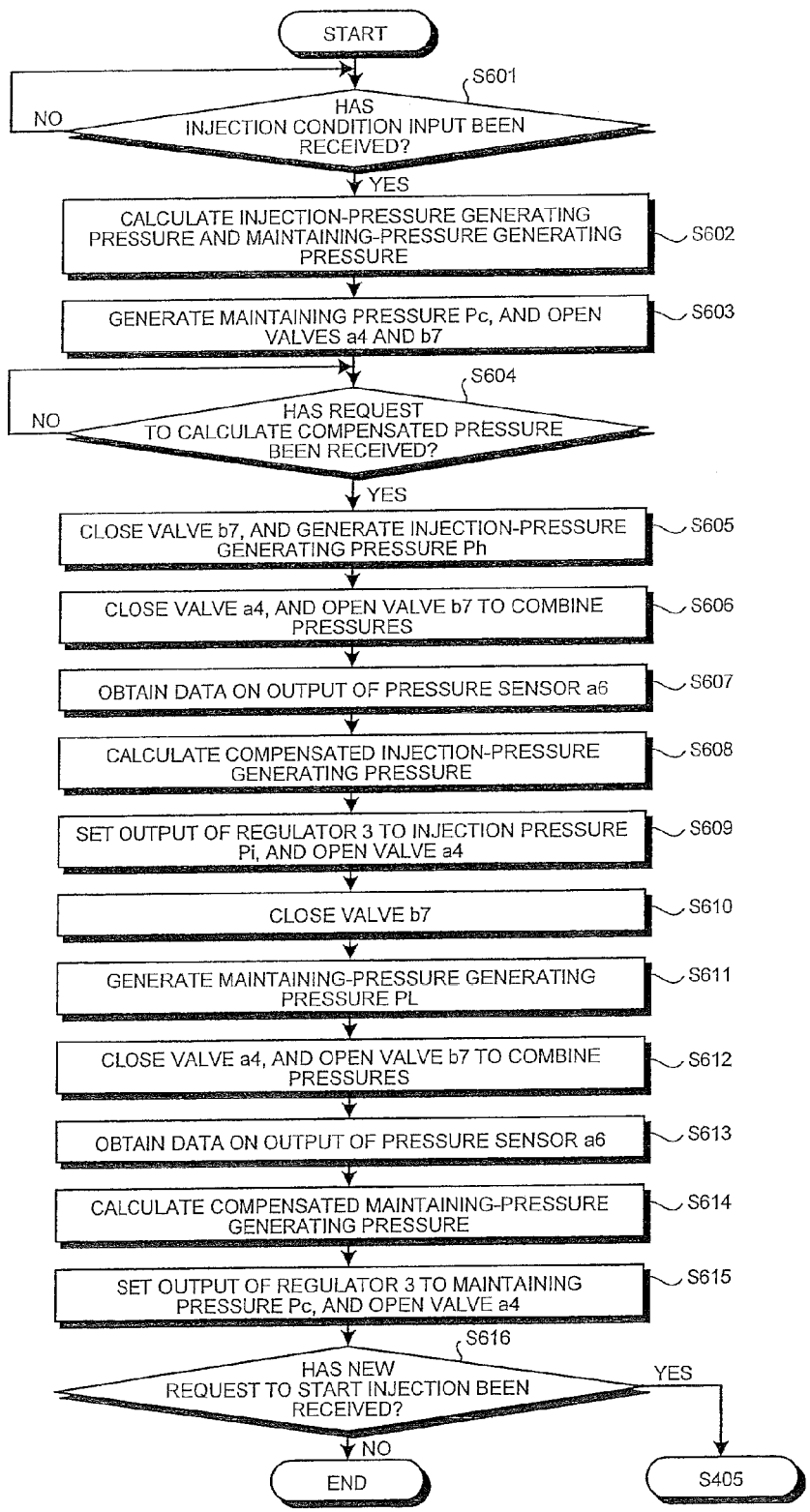
FIG. 6 is flowchart of a process performed by the liquid discharge volume control device according to the second embodiment.

FIG. 6 is a flowchart of a process procedure performed by the liquid discharge volume control device according to the second embodiment.

First, when the liquid-discharge-volume control device 20 of the second embodiment receives a new operator input on various conditions (e.g., a liquid discharge volume to be set based on the injection pressure Pi and a pressure-application time, and the maintaining pressure Pc to be set based on the viscosity of a liquid filled in the capillary 9, and the like) pertaining to injection via a keyboard or a mouse (YES at step S601), the same process at steps S402 to S403 in FIG. 3 as described previously in the first embodiment is performed (steps S602 to S603).

Subsequently, the liquid-discharge-volume control device 20 of the second embodiment maintains the state until an operator request to calculate a compensated injection-pressure generating pressure and a compensated maintaining-pressure generating pressure-compensating pressure is received (NO at step S604).

On the other hand, when the liquid-discharge-volume control device 20 of the second embodiment receives an operator calculation request to calculate a compensated injection-pressure generating pressure and a compensated maintaining-pressure generating pressure-compensating pressure (YES at step S604), the valve b7 controller 264 closes the valves b7, and the regulator-output-pressure controller 262 causes the regulator 3 to generate the injection-pressure generating pressure Ph by using the positive pressure pump 1 and the negative pressure pump 2 (step S605).

While the valve a4 controller 263 closes the valve a4 to maintain the regulating chamber 5 under the injection-pressure generating pressure Ph, the valve b7 controller 264 opens the valve b7 to combine the injection-pressure generating pressure Ph with the maintaining pressure Pc. The newly-generated combined pressure is applied to the capillary 9 (step S606).

The pressure sensor-output detector 261 obtains the actual value Pi' of the newly-generated combined pressure, and the like, and stores the values in the pressure sensor-output storage unit 251 (step S607). The volume-ratio calculating unit 241 calculates the injection-pressure-compensating volume ratio $\eta i$ using the actual value stored in the pressure sensor-output storage unit 251, and the injection-pressure-generating-pressure calculating unit 242 calculates the compensated injection-pressure generating pressure Ph' using the injection-pressure-compensating volume ratio $\eta i$ (step S608).

Subsequently, while the regulator-output-pressure controller 262 causes the regulator 3 to generate the injection pressure Pi by using the positive pressure pump 1 and the negative pressure pump 2, the valve a4 controller 263 opens the valve a4 (step S609).

While the valve b7 controller 264 closes the valves b7 (step S610) to maintain the capillary 9 under the injection pressure Pi, the regulator-output-pressure controller 262 causes the regulator 3 to generate the maintaining-pressure generating pressure PL by using the positive pressure pump 1 and the negative pressure pump 2 (step S611).

While the valve a4 controller 263 closes the valve a4 to maintain the regulating chamber 5 under the maintaining-pressure generating pressure PL, the valve b7 controller 264 opens the valve b7 to combine the maintaining-pressure generating pressure PL with the injection pressure Pi. The newly-generated combined pressure is applied to the capillary 9 (step S612).

The pressure sensor-output detector 261 obtains an actual value Pc' of the newly-generated combined pressure, and the like, and stores the values in the pressure sensor-output storage unit 251 (step S613). The volume-ratio calculating unit 241 calculates the maintaining-pressure-compensating volume ratio $\eta c$ using the actual value stored in the pressure sensor-output storage unit 251, and the maintaining-pressure-generating-pressure calculating unit 243 calculates the compensated maintaining-pressure generating pressure PL' using the maintaining-pressure-compensating volume ratio $\eta c$ (step S614).

While the regulator-output-pressure controller 262 causes the regulator 3 to generate the maintaining pressure Pc by using the positive pressure pump 1 and the negative pressure pump 2, the valve a4 controller 263 opens the valve a4 (step S615).

Upon receipt of an operator request to start injection (YES at step S616), the liquid-discharge-volume control device 20 of the second embodiment performs the process pertaining to step S405 and subsequent steps. When a new request for injection start is not issued (NO at step S616), the process ends.

As explained above, according to the second embodiment, an injection-pressure generating pressure is compensated by detecting an actual value of pressure output from the regulator 3 as the injection-pressure generating pressure with the pressure sensor a6, an actual value of pressure applied to the capillary 9 as a maintaining pressure with the pressure sensor a6 immediately before the valve b7 is closed, and a value of a combined pressure generated by opening the valve b7 with the pressure sensor a6; and a maintaining-pressure generating pressure is compensated by detecting an actual value of pressure output from the regulator 3 as the maintaining-pressure generating pressure with the pressure sensor a6, an actual value of pressure applied to the capillary 9 as an injection pressure with the pressure sensor a6 immediately before the valve b7 is closed, and a value of a generated combined pressure with the pressure sensor a6. Therefore, it is possible to recalculate a value of pressure to be output from the regulator 3 to generate a renewed injection pressure or a renewed maintaining pressure based on the actual pressure values taken for each injection setting condition, thereby achieving stabilization of a liquid discharge volume under any setting condition.

Figure 7:
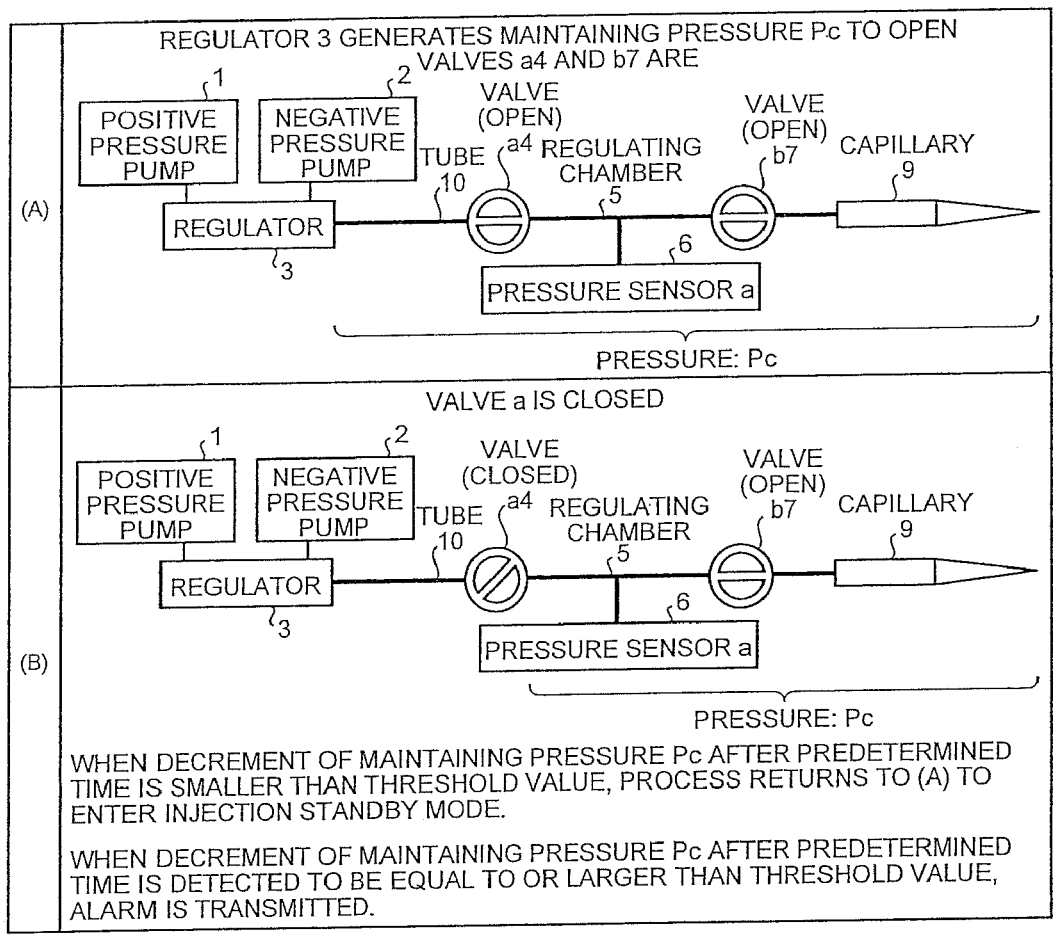
FIG. 7 is a schematic for explaining an overview and features of a liquid discharge volume control device according to a third embodiment of the present invention.

FIG. 7 is a schematic for explaining an overview and features of a liquid-discharge-volume control device 30 according to a third embodiment of the present invention. The liquid-discharge-volume control device 30 is basically similar to the liquid discharge volume control device 20 except for its function of detecting air leakage. Therefore, the same explanation is not repeated.

As with the liquid discharge volume control device 20, the liquid-discharge-volume control device 30 calculates the injection-pressure generating pressure Ph and the maintaining-pressure generating pressure PL based on the injection pressure Pi and the maintaining pressure Pc, which are input by an operator, using the already-calculated volume ratio η and equation (3) of FIG. 13. The liquid-discharge-volume control device 20 causes the regulator 3 to generate the maintaining pressure Pc by using the positive pressure pump 1 and the negative pressure pump 2, and then opens the valves a4 and b7 (see (A) of FIG. 7).

Subsequently, as shown in (B) of FIG. 7, the liquid discharge volume control device closes the valve a4, acquires a value of pressure applied to the capillary 9 after a predetermined period of time (e.g., after one minute) from the pressure sensor a6, and subtracts the pressure value from the maintaining pressure Pc to obtain a decrement. When the decrement is smaller than a set threshold value, the liquid discharge volume control device determines that no air leakage has occurred. The liquid-discharge-volume control device 20 causes the regulator 3 to generate the maintaining pressure Pc by using the positive pressure pump 1 and the negative pressure pump 2, and then opens the valves a4 and b7 to return to the state shown in (A) of FIG. 7, where the liquid-discharge-volume control device 20 waits while maintaining the state until receipt of a request to start injection.

On the other hand, when the calculated decrement is equal to or larger than the set threshold value, the liquid discharge volume control device determines that air leakage has occurred, and transmits an alarm of this effect to the microinjection apparatus 100. This alarm allows an operator to avoid starting injection in a state where air leakage has occurred due to poor connection of the capillary 9 or deterioration of the tube 10.

As explained above, because the liquid discharge volume control device of the third embodiment is capable of detecting air leakage due to poor connection of a capillary or deterioration of a tube during preparation prior to injection, it is possible to avoid performing injection in a state where a liquid discharge volume is unstable due to the air leakage.

Figure 8:
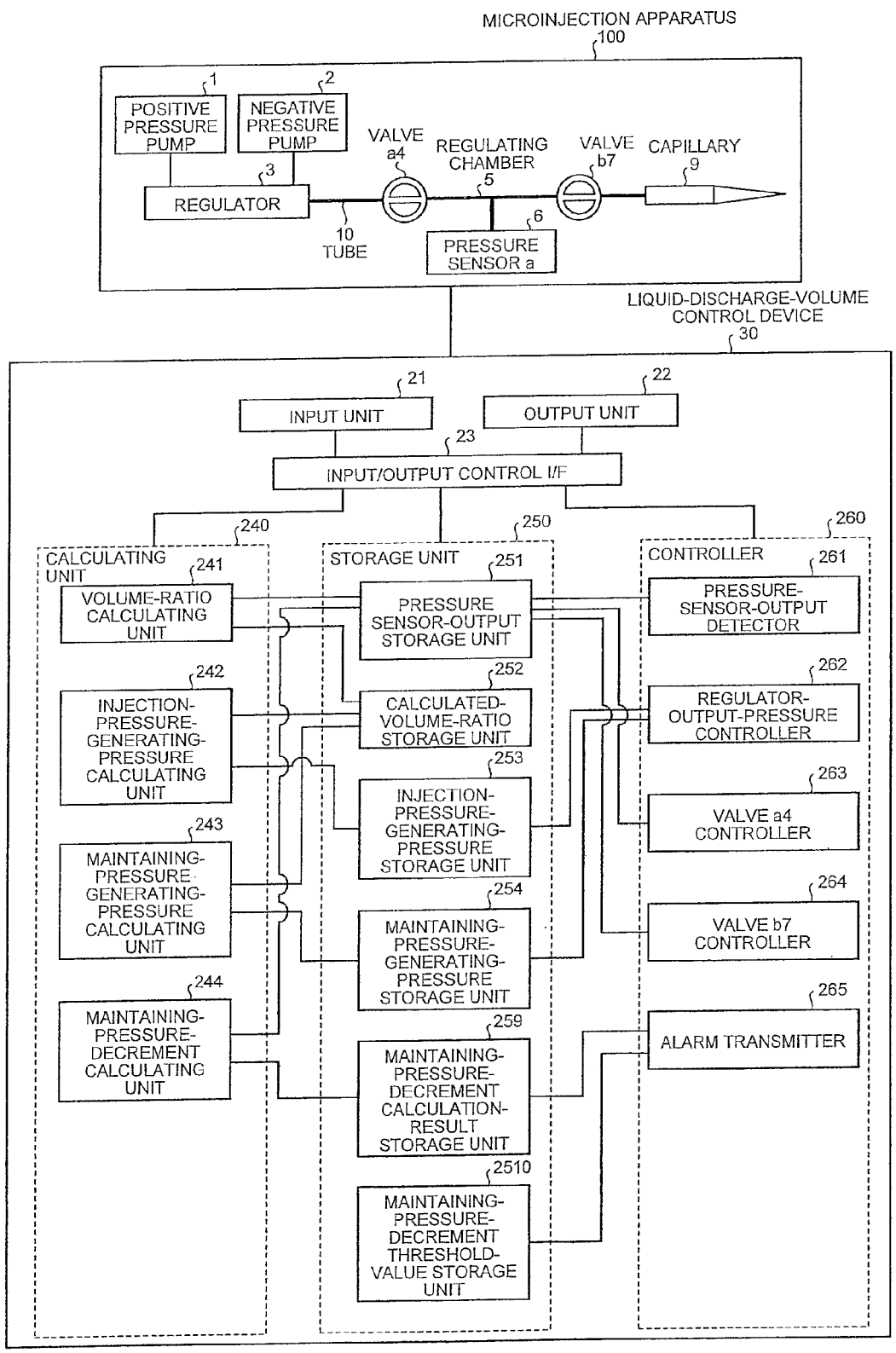
FIG. 8 is a block diagram of the liquid discharge volume control device according to the third embodiment.

FIG. 8 is a block diagram of the liquid-discharge-volume control device 30. The liquid-discharge-volume control device 30 includes a calculating unit 240, a storage unit 250, and a controller 260 in place of the calculating unit 24, the storage unit 25, and the controller 26. The calculating unit 240 further includes a maintaining-pressure-decrement calculating unit 244. The storage unit 250 further includes a maintaining-pressure-decrement calculation-result storage unit 259, and a maintaining-pressure-decrement threshold-value storage unit 2510. The controller 260 further includes an alarm transmitter 265.

As shown in (B) of FIG. 7, the maintaining-pressure-decrement calculating unit 244 retrieves a value of pressure applied to the capillary 9 from the pressure sensor-output storage unit 251 after a lapse of a predetermined time (e.g., after one minute) since the valve a4 is closed. The maintaining-pressure-decrement calculating unit 244 subtracts the pressure value from the maintaining pressure Pc to obtain a decrement, and stores the calculation result in the maintaining-pressure-decrement calculation-result storage unit 259.

The maintaining-pressure-decrement threshold-value storage unit 2510 stores therein a set threshold value to be used in a process performed by the alarm transmitter 265, described later. Specifically, the maintaining-pressure-decrement threshold-value storage unit 2510 stores therein a set threshold value for use in determination as to whether air leakage has occurred.

The alarm transmitter 265 compares the decrement stored in the maintaining-pressure-decrement calculation-result storage unit 259 and the set threshold value stored in the maintaining-pressure-decrement threshold-value storage unit 2510. When the decrement is equal to or larger than the set threshold value, the alarm transmitter 265 determines that air leakage has occurred, and transmits an alarm of this effect to the microinjection apparatus 100. The alarm allows an operator to avoid starting injection in a state where air leakage has occurred due to poor connection of the capillary 9 or deterioration of the tube 10.

Figure 9:
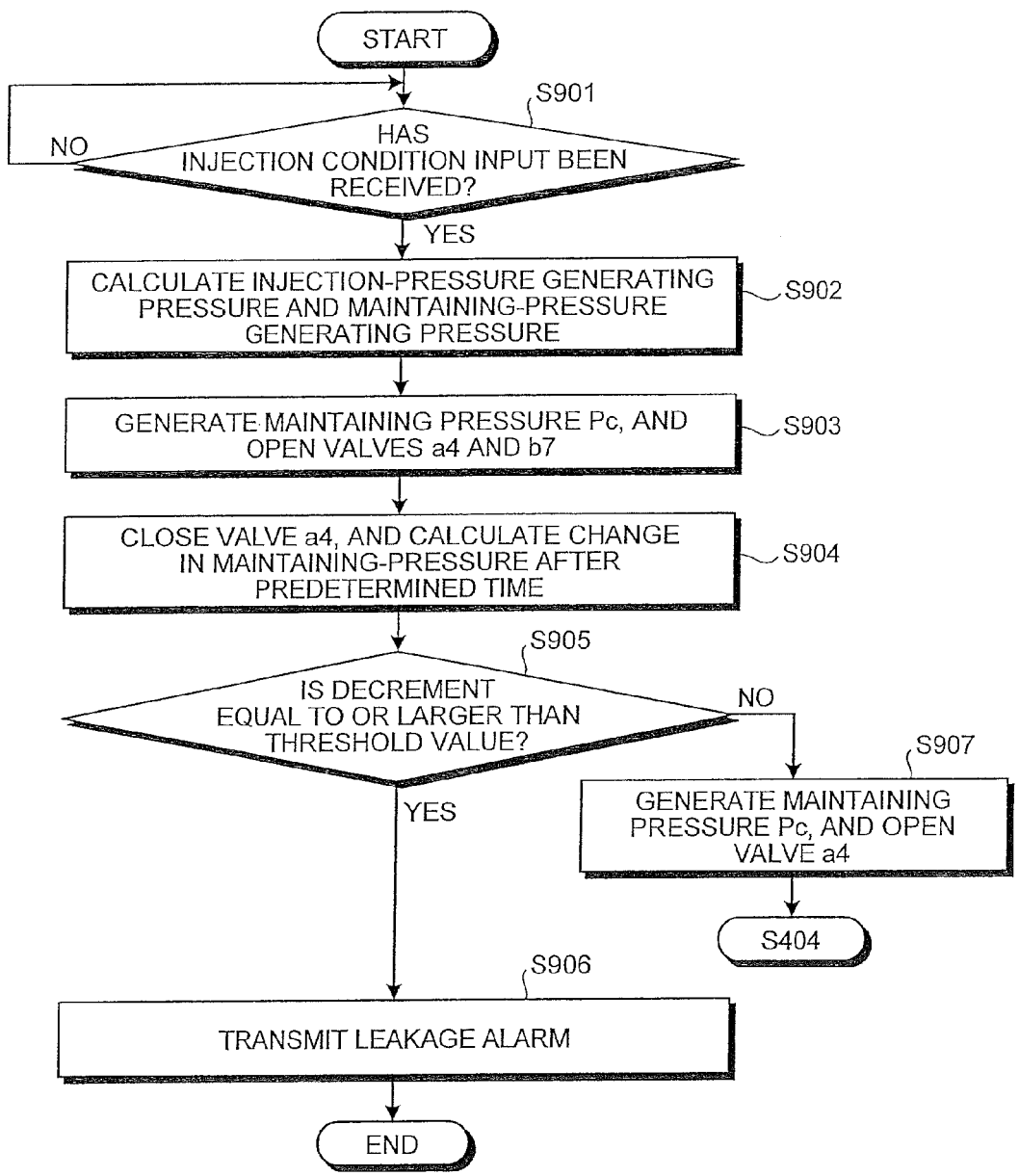
FIG. 9 is a flowchart of a process performed by the liquid discharge volume control device shown in FIG. 8.

FIG. 9 is a flowchart of a process procedure performed by the liquid-discharge-volume control device 30.

First, when the liquid-discharge-volume control device 30 receives a new operator input on various conditions (e.g., a liquid discharge volume to be set based on the injection pressure Pi and a pressure-application time, and the maintaining pressure Pc to be set based on the viscosity of a liquid filled in the capillary 9, and the like) pertaining to injection via a keyboard or a mouse (YES at step S901), the same process at steps S402 to S403 in FIG. 3 as described in the first embodiment is performed (steps S902 to S903).

Subsequently, the valve a4 controller 263 closes the valve a4, retrieves a value of pressure applied to the capillary 9 from the pressure sensor-output storage unit 251 after a lapse of a predetermined time (e.g., after one minute) since the valve a4 is closed, and subtracts the pressure value from the maintaining pressure Pc to obtain a decrement (step S904).

The alarm transmitter 265 compares the decrement and the set threshold value, thereby determining whether the decrement is equal to or larger than the set threshold value (step S905). When the decrement is smaller than the set threshold value (NO at step S905), while the regulator-output-pressure controller 262 causes the regulator 3 to generate the maintaining pressure Pc by using the positive pressure pump 1 and the negative pressure pump 2, the valve a4 controller 263 opens the valve a4 (step S907) to maintain a state where the capillary 9 receives the maintaining pressure Pc. The liquid-discharge-volume control device 30 waits while maintaining this state until receipt of a request to start injection (see step S404 shown in FIG. 4).

On the other hand, when the calculated decrement is equal to or larger than the set threshold value (YES at step S905), the alarm transmitter 265 determines that air leakage has occurred, and transmits an alarm of this effect to the microinjection apparatus 100 (step S906), and the process ends.

As explained above, according to the third embodiment, the valve a4 is closed while the maintaining pressure generated by the regulator 3 upon opening of the valves a4 and b7 is being applied to the capillary 9. Then, the pressure sensor a6 measures a change in the maintaining pressure during a predetermined time period after the valve a4 is closed to detect pressure leakage. Therefore, air leakage due to poor connection of the capillary 9 or deterioration of the tube 10 can be detected during preparation prior to injection. Thus, it is possible to avoid performing injection in a state where a liquid discharge volume is unstable due to air leakage.

In the first to third embodiments, the microinjection apparatus 100 includes the tube 10 of which volume changes depending on the magnitude of pressure applied thereto. However, the invention is not so limited, and the tube 10 in the microinjection apparatus 100 can be formed of a material that exhibits no volume change. In this case, volumetric change of the tube 10 that connects the regulating chamber 5, the valves a4 and b7, the capillary 9, and the like, can be suppressed, thereby achieving stabilization of a liquid discharge volume.

In the first and third embodiments, the injection-pressure generating pressure Ph and the maintaining-pressure generating pressure PL are calculated from the injection pressure Pi and the maintaining pressure Pc, which are input by an operator, based on a volume ratio having been calculated and stored. However, the present invention is not so limited, and, for example, it is possible to use a table that contains values of the injection-pressure generating pressure Ph corresponding to various injection pressures Pi obtained from calculation based on a volume ratio, and values of the maintaining-pressure generating pressure PL corresponding to various maintaining pressures Pc obtained from calculation based on a volume ratio. An operator selects an injection pressure and a maintaining pressure from a list of the table. The liquid-discharge-volume control device refers to the table, and associates the selected injection pressure and the maintaining pressure to an injection-pressure generating pressure and a maintaining-pressure generating pressure, respectively.

While, in the above embodiments, the microinjection apparatus is controlled, the present invention is so not limited, and can be applied to any liquid dispensing apparatus that consecutively dispenses a given volume of liquid as well.

While, in the above embodiments, "solution" is discharged into a "cell", the present invention is not so limited, and can be applied to the case that "gas" is discharged into a "microstructure".

Of the processes described in the embodiments, all or part of the processes explained as being performed automatically can be performed manually (for example, occurrence of air leakage can be determined when an operator inputs a request to start injection, instead of determining the air leakage after a lapse of a predetermined time). Similarly, all or part of the processes explained as being performed manually can be performed automatically by a known method. The processing procedures, specific names, various data, and information including parameters described in the embodiments or shown in the drawings can be changed as required unless otherwise specified. For example, the calculation of the compensated injection-pressure generating pressure (step S608) can be started at the same time of calculating the compensated maintaining-pressure generating pressure (step S613).

The constituent elements of each device shown in the drawings are functionally conceptual, and need not be physically configured as illustrated. In other words, the specific mode (for example, the mode of FIG. 3) of separation and integration of the constituent elements is not limited to those shown in the drawings. The constituent elements, as a whole or in part, can be separated or integrated either functionally or physically based on various types of loads or use conditions, for example, the injection-pressure-generating-pressure calculating unit 242 can be integrated with the maintaining-pressure-generating-pressure calculating unit 243. The process functions performed by each device are entirely or partially realized by a central processing unit (CPU) or computer programs that are analyzed and executed by the CPU, or realized as wired-logic hardware.

Figure 10:
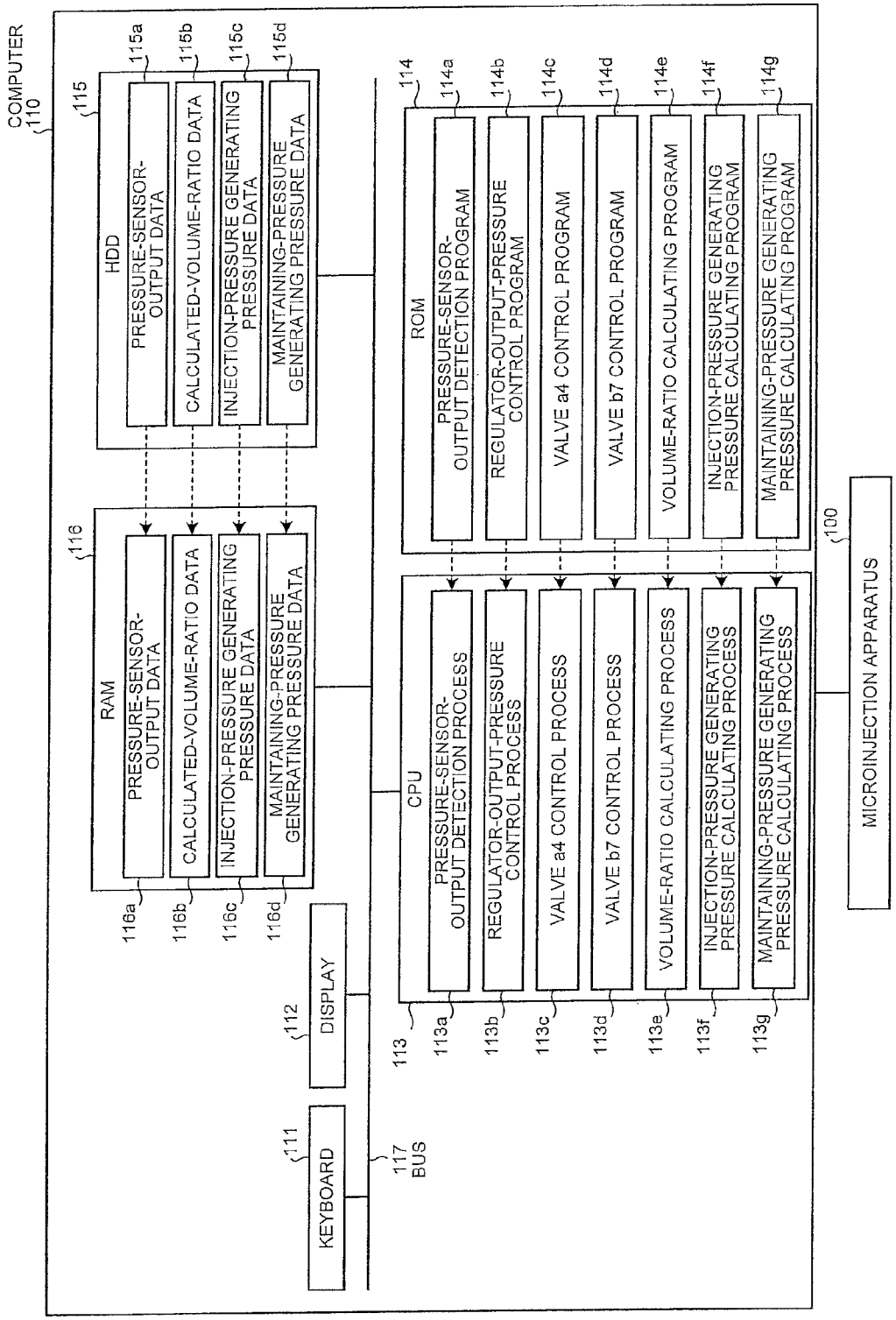
FIG. 10 is a diagram of a computer that executes a computer program to implement the liquid discharge volume control device shown in FIG. 1.

The liquid-discharge-volume control device is explained above as hardware; however, it can be implemented as software. In other words, a computer program (hereinafter, a liquid discharge volume control program) can be executed on a computer to realize the same function as the liquid-discharge-volume control device. In the following, such a computer that execute the liquid discharge volume control program to realize the same function as the liquid-discharge-volume control device 20 in the first embodiment is explained. FIG. 10 is a diagram of a computer 110 that executes the liquid discharge volume control program.

The computer 110 includes a keyboard 111, a display 112, a CPU 113, a read only memory (ROM) 114, a hard disk drive (HDD) 115, and a random access memory (RAM) 116 and the like, which are connected by a bus 117. The computer 110 is further connected to the microinjection apparatus 100.

In the ROM 114, the liquid discharge volume control program that fulfils the same function as the liquid-discharge-volume control device 20 explained in the first embodiment. That is, as shown in FIG. 10, a pressure sensor-output detection program 114*a*, a regulator-output-pressure control program 114*b*, a valve a4 control program 114*c*, a valve b7 control program 114*d*, a volume-ratio calculating program 114*e*, an injection-pressure generating pressure calculating program 114*f*, and a maintaining-pressure generating pressure calculating program 114*g*, are stored in advance. The programs 114*a* to 114*g* can be integrated or distributed as required.

The CPU 113 reads the programs 114*a* to 114*g* from the ROM 114 and executes the programs. Hence, the programs 114*a* to 114*g* function as a pressure sensor-output detection process 113*a*, a regulator-output-pressure control process 113*b*, a valve a4 control process 113*c*, a valve b7 control process 113*d*, a volume-ratio calculating process 113*e*, an injection-pressure generating pressure calculating process 113*f*, and a maintaining-pressure generating pressure calculating process 113*g*. The processes 113*a* to 113*g* correspond to the pressure sensor-output detector 261, the regulator-output-pressure controller 262, the valve a4 controller 263, the valve b7 controller 264, the volume-ratio calculating unit 241, the injection-pressure-generating-pressure calculating unit 242, and the maintaining-pressure-generating-pressure calculating unit 243 shown in FIG. 2.

The HDD 115 includes pressure sensor-output data 115*a*, calculated-volume-ratio data 115*b*, injection-pressure generating pressure data 115*c*, and maintaining-pressure generating pressure data 115d. The pressure sensor-output data 115a corresponds to the pressure sensor-output storage unit 251 explained with reference to FIG. 3, the calculated-volume-ratio data 115b corresponds to the calculated-volume-ratio storage unit 252, the injection-pressure generating pressure data 115c corresponds to the injection-pressure generating pressure storage unit 253, and the maintaining-pressure generating pressure data 115d corresponds to the maintaining-pressure generating pressure storage unit 254. The CPU 113 stores the pressure sensor-output data 115a as pressure sensor-output data 116a, the calculated-volume-ratio data 115b as calculated-volume-ratio data 116b, the injection-pressure generating pressure data 115c as injection-pressure generating pressure data 116c, and the maintaining-pressure generating pressure data 115d as maintaining-pressure generating pressure data 116d. The CPU 113 performs the process pertaining to the liquid discharge volume control using the pressure sensor-output data 116a, the calculated-volume-ratio data 116b, the injection-pressure generating pressure data 116c, and the maintaining-pressure generating pressure data 116d.

The programs 114a to 114g do not need to be stored initially in the ROM 114, and for example, the programs can be stored in a portable physical medium connected to the computer 110, such as a flexible disk (FD), a compact disc-read only memory (CD-ROM), a magneto optical disk (MO), a digital versatile disk (DVD), or an integrated circuit (IC) card, or a fixed physical medium inside or outside the computer 110 such as HDD. The programs can also be stored in another computer (or a server) connected to the computer 110 via a public line, the Internet, a local area network (LAN), or a wide area network (WAN), and downloaded.

As set forth hereinabove, according to an embodiment of the present invention, a pressure output to a capillary can be detected without installing another pressure sensor for detecting the pressure. Thus, facility investment can be reduced can be reduced.

Moreover, volume change in a tube that connects a regulating chamber, valves, a capillary, and the like, can be suppressed. Thus, stabilization of a liquid discharge volume can be achieved.

Although the invention has been described with respect to a specific embodiment for a complete and clear disclosure, the appended claims are not to be thus limited but are to be construed as embodying all modifications and alternative constructions that may occur to one skilled in the art that fairly fall within the basic teaching herein set forth.

What is claimed is:

1. An injecting apparatus that injects an object into a microbody, the injecting apparatus comprising:
   a capillary that injects the object into the microbody;
   a regulator that regulates pressure to be applied to the object;
   a first valve that is located in a passage between the capillary and the regulator;
   a second valve that is located between the first valve and the regulator; and
   a controller that controls the regulator, the first valve, and the second valve, wherein
   the controller closes the first valve in a state where pressure in the capillary is maintained at a first pressure, causes the regulator to generate a second pressure, closes the second valve, opens the first valve to combine the first pressure with the second pressure to generate a third pressure, applies the third pressure to the capillary to cause discharge of the object from the capillary, and causes the regulator to reset the third pressure while the object is being discharged from the capillary.

2. A discharge volume control device that controls a microinjection apparatus, the microinjection apparatus including a regulator that regulates and outputs pressure, a capillary that is filled with an object to be discharged and connected to the regulator by a tube, a first valve that is located on regulator side in the tube and a second valve that is located on capillary side in the tube, and controls volume of the object discharged from the capillary, the discharge volume control device comprising:
   a controller that opens the second valve from a state where the first valve and the second valve are closed to combine an injection-pressure generating pressure with a maintaining pressure to generate an injection pressure, the injection-pressure generating pressure being retained between the first valve and the second valve to generate the injection pressure that causes the object to be discharged from the capillary, and the maintaining pressure having been applied to the capillary to prevent backflow of the object into the capillary, applies the injection pressure to the capillary to cause discharge of the object from the capillary, sets an output pressure of the regulator to the injection pressure, and opens the first valve to reapply the injection pressure to the capillary,
   wherein the controller opens the second valve from a state where the first valve and the second valve are closed to combine a maintaining-pressure generating pressure with the injection pressure having been applied to the capillary to generate the maintaining pressure, the maintaining-pressure generating pressure being retained between the first valve and the second valve to generate the maintaining pressure, applies the maintaining pressure to the capillary to terminate the discharge of the object, sets the output pressure of the regulator to the maintaining pressure, and opens the first valve to reapply the maintaining pressure to the capillary.

3. A computer-readable recording medium that stores therein a computer program for controlling a microinjection apparatus, the microinjection apparatus including a regulator that regulates and outputs pressure, a capillary that is filled with an object to be discharged and connected to the regulator by a tube, a first valve that is located on regulator side in the tube and a second valve that is located on capillary side in the tube, and controlling volume of the object discharged from the capillary, the computer program causing a computer to execute:
   opening the second valve from a state where the first valve and the second valve are closed to combine an injection-pressure generating pressure with a maintaining pressure to generate an injection pressure, the injection-pressure generating pressure being retained between the first valve and the second valve to generate the injection pressure that causes the object to be discharged from the capillary, and the maintaining pressure having been applied to the capillary to prevent backflow of the object into the capillary;
   applying the injection pressure to the capillary to cause discharge of the object from the capillary;
   setting an output pressure of the regulator to the injection pressure;
   opening the first valve to reapply the injection pressure to the capillary;
   opening the second valve from the state where the first valve and the second valve are closed to combine a maintaining-pressure generating pressure with the injection pressure having been applied to the capillary to generate the maintaining pressure, the maintaining-pressure generating pressure being retained between the first valve and the second valve to generate the maintaining pressure;

applying the maintaining pressure to the capillary to terminate the discharge of the object;

setting the output pressure of the regulator to the maintaining pressure; and opening the first valve to reapply the maintaining pressure to the capillary.

* * * * *